US012799493B2

(12) United States Patent
Trepotec et al.

(10) Patent No.: US 12,799,493 B2
(45) Date of Patent: Nov. 17, 2026

(54) PLASMID CONTAINING A SEQUENCE ENCODING AN mRNA WITH A SEGMENTED POLY(A) TAIL

(71) Applicant: ethris GmbH, Planegg (DE)

(72) Inventors: Zeljka Trepotec, Munich (DE); Manish Kumar Aneja, Munich (DE); Carsten Rudolph, Krailling (DE); Christian Plank, Wessling (DE); Ludwig Weiss, Kissing (DE)

(73) Assignee: ethris GmbH, Planegg (DE)

( * ) Notice: Subject to any disclaimer, the term of this patent is extended or adjusted under 35 U.S.C. 154(b) by 1004 days.

(21) Appl. No.: 17/284,779

(22) PCT Filed: Oct. 10, 2019

(86) PCT No.: PCT/EP2019/077477
§ 371 (c)(1),
(2) Date: Apr. 12, 2021

(87) PCT Pub. No.: WO2020/074642
PCT Pub. Date: Apr. 16, 2020

(65) Prior Publication Data

US 2021/0348172 A1 Nov. 11, 2021

(30) Foreign Application Priority Data

Oct. 11, 2018 (EP) .................................... 18199857

(51) Int. Cl.
*C12N 15/68* (2006.01)
*A61K 48/00* (2006.01)
*C12N 15/11* (2006.01)

(52) U.S. Cl.
CPC .......... *C12N 15/68* (2013.01); *A61K 48/0066* (2013.01); *C12N 2830/50* (2013.01)

(58) Field of Classification Search
None
See application file for complete search history.

(56) References Cited

U.S. PATENT DOCUMENTS

| | | | |
|---|---|---|---|
| 2004/0031072 A1 | 2/2004 | La Rosa et al. |
| 2004/0123343 A1 | 6/2004 | La Rosa et al. |

FOREIGN PATENT DOCUMENTS

| | | | |
|---|---|---|---|
| CN | 105 734 053 A | 7/2006 |
| CN | 105505755 A | 4/2016 |
| RU | 2497949 C2 | 11/2013 |
| WO | WO 2005/012875 A2 | 2/2005 |
| WO | WO 2005/012875 A3 | 2/2005 |
| WO | 2007/038276 A2 | 4/2007 |
| WO | WO-2016/005324 A1 | 1/2016 |
| WO | WO 2017/001554 A1 | 1/2017 |

OTHER PUBLICATIONS

Thermo-Fischer Scientific, The Basiics In Vitro Transcription, pp. 1-9, downloaded Mar. 28, 2025.*
Ibraheem et al., "Gene Therapy and DNA Delivery Systems," *International Journal of Pharmaceutics* 459(1-2):70-83, E-pub Nov. 25, 2013.
Nemtsova et al., "Official Medications for Anti-tumor Gene Therapy," *Research and Practical Medicine Journal* 3(4):33-43, 2016, with the English translation.
Grier, Alexandra E., et al. "pEVL: A linear plasmid for generating mRNA IVT templates with extended encoded poly (A) sequences." *Molecular Therapy-Nucleic Acids* 5, E306 (2016): pp. 1-10.
Chang, Hyeshik, et al. "TAIL-seq: genome-wide determination of poly (A) tail length and 3' end modifications." *Molecular cell* 53.6 (2014): 1044-1052.
Beverly, Michael, Caitlin Hagen, and Olga Slack. "Poly A tail length analysis of in vitro transcribed mRNA by LC-MS." *Analytical and bioanalytical chemistry* 410.6 (2018): 1667-1677.
Trepotec, Zeljka, et al. "Segmented poly (A) tails significantly reduce recombination of plasmid DNA without affecting mRNA translation efficiency or half-life." *RNA* 25.4 (2019): 507-518.
Ustyantsev, I.G., et al., "Canonical and Noncanonical RNA Polyadenylation," Molecular Biology, 51(2): 226-236 (2017).
Ferizi, M., et al., "mRNA Engineering Strategies to Improve mRNA Translation and Stability for Musculoskeletal Gene Therapy," ORS Annual Meeting Poster No. 0752, 2017, Molecular Therapy, 22(1) Abstract No. 114, p. S43 (2014).
Ikegami, M., et al., "Enhanced Transfection of MRNA Transcribed From Elongated-poly(A/T) Tail-Containing Vector," Mol. Ther. Nucleic Acids, 5(4): 1-10 (2016).
Godiska et al., "Linear plasmid vector for cloning of repetitive or unstable sequences in *Escherichia coli," Nucleic Acids Research* 38(6):e88 (9 pages), E-pub Dec. 29, 2009.

* cited by examiner

*Primary Examiner* — Maria Marvich
(74) *Attorney, Agent, or Firm* — Klarquist Sparkman, LLP; Susan Alpert Siegel; Gregory K. Scott

(57) ABSTRACT

The present disclosure provides a DNA plasmid comprising a sequence which encodes an mRNA molecule and a modified poly(A) tail, wherein the part of the sequence that encodes the modified poly(A) tail is characterized in that it consists of at least two A elements each defined as a nucleotide sequence consisting of 55 to 65 T nucleotides and at least one S element each S element consisting of one nucleotide that is not a T nucleotide, or 2 to 10 nucleotides, preferably 6 nucleotides, wherein each of the two terminal nucleotides is not a T nucleotide, wherein the number of A elements is one more than the number of S elements, and wherein any two A elements are separated by one S element; said DNA plasmid exhibiting a reduced recombination during amplification in a bacterial host cell compared to the same DNA plasmid without said at least one S element.

18 Claims, 3 Drawing Sheets

Figure 1:
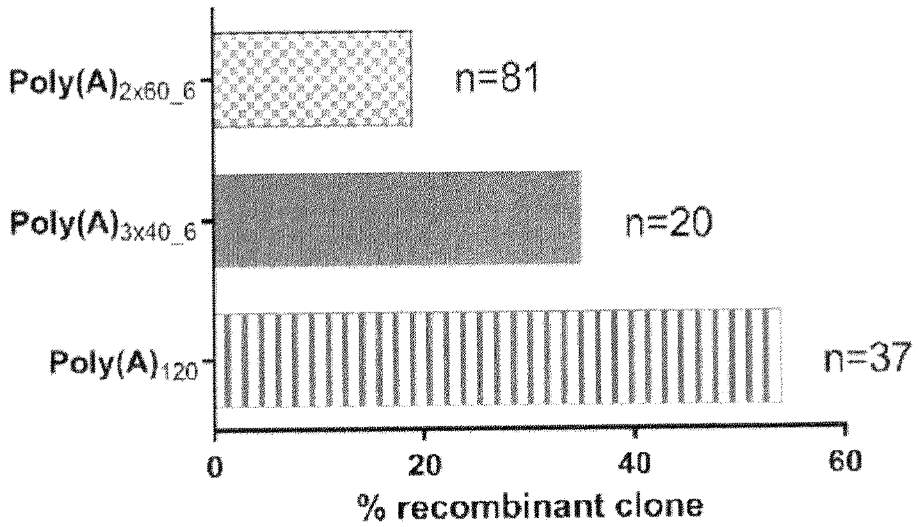

Specification includes a Sequence Listing.

PLASMID CONTAINING A SEQUENCE ENCODING AN mRNA WITH A SEGMENTED POLY(A) TAIL

RELATED APPLICATIONS

This application is a national stage filing under 35 U.S.C. 371 of International Application No. PCT/EP2019/077477, filed Oct. 10, 2019, which claims the benefit of EP Application No. 18199857.6, filed on Oct. 11, 2018. The entire teachings of the above applications are incorporated herein by reference. International Application No. PCT/EP2019/077477 was published under PCT Article 21(2) in English.

The present invention relates to a DNA plasmid comprising a DNA sequence which contains a first nucleotide sequence which encodes an mRNA molecule and, located downstream thereof, a second nucleotide sequence which encodes a modified poly(A) tail, wherein said second nucleotide sequence is characterized in that it consists of at least two A elements each defined as a nucleotide sequence consisting of 55 to 65 T nucleotides and at least one S element each S element consisting of i) one nucleotide that is not a T nucleotide, or ii) 2 to 10 nucleotides, preferably 6 nucleotides, wherein each of the two terminal nucleotides is not a T nucleotide, wherein the total number of A elements is one more than the total number of S elements, and wherein any two A elements are separated by one S element.

Genetic information is stored as deoxyribonucleic acid (DNA) in the cell and can be transcribed into ribonucleic acid (RNA) when required. Both, DNA and RNA molecules, are built up of nucleotides consisting of a nitrogenous base, a five-carbon sugar, and at least one phosphate group. Different types of RNA molecules exist including mRNA molecules that carry the genetic information for protein synthesis. In eukaryotes, these mRNA molecules are transcribed from the DNA as pre-mature mRNA molecules and subsequently modified by adding for example a 3' polyadenosine (poly(A)) tail. The poly(A) tail is characteristic for mature, functional mRNA molecules with one of the few known exceptions being histone mRNAs (Marzluff et al., 2008, Nat. Rev. Genet., 9(11):843-854; Yang et al., 2011, Genome Biology, 12:R16). The mature mRNA molecule is then transferred from the cell nucleus into the cytoplasm where it is translated into proteins. Thus, the DNA sequence as well as the amount, stability and translational efficiency of the mature mRNA molecule mainly determine the synthesis of the respective protein in a cell.

For optimizing the synthesis of a desired protein in a cell, for example in therapeutic contexts, mRNA based approaches represent a promising tool. The use of mRNA molecules has the advantage that the molecules have to be introduced only into the cytoplasm of a cell for protein translation (Tavernier et al., 2011, J Control Release, 150 (3):238-247; Yamamoto et al., 2009, Eur J Pharm Biopharm, 71(3):484-489). Compared to the use of the respective DNA sequence comprised in an appropriate carrier such as a plasmid, the use of mRNA molecules is furthermore less difficult, more efficient, and avoids the considerable risk of chromosomal DNA being altered if the plasmid or parts thereof become incorporated into the genome. Initial challenges associated with introducing mRNA molecules into cells such as the instability of mRNA molecules and immune responses have been successfully met using for example chemically modified nucleotides (WO 2011/012316; EP patent application number 18 15 6466.7; KarikO et al., 2008, Mol. Ther., 16(11):1833-40). Several determinants of mRNA efficiency have been identified and investigated so far, including the efficiency of 5' capping and the composition of the 5' cap, the nature of untranslated regions, codon optimization of protein coding sequences, the presence of miRNA target sequences in the protein coding sequence and untranslated regions, and the length of the 3' poly(A) tail (e.g. Thess, et al., 2015, Mol. Ther., 23(9), 1456-1464; Trepotec et al., 2018, Tissue Engineering. Part A, ten.TEA.2017.0485; Ziemniak et al., 2013, Future Med. Chem., 5(10), 1141-1172).

For improving the efficiency of mRNA based approaches, optimizing the length of the poly(A) tail is crucial. The length of the poly(A) tail is considered as major determinant of mRNA turnover as the degradation of the poly(A) tail is the first step in mRNA decay before either 5' cap hydrolysis or further 3' to 5' degradation occurs (e.g. reviewed in Lodish et al., Mol. Cell Biol. 4$^{th}$ edition, New York: W. H. Freeman, 2000, Section 11.2; Ramanathan et al., 2016, Nucleic Acids Res., 44(16): 7511-7526). In mammals for example, poly(A) tails have been reported to have an average length of approximately 200 to 300 nucleotides. Furthermore, it has been reported that poly(A) tails can exhibit terminal nucleotides other than A nucleotides and that for example a terminal G nucleotide can retard the degradation of the poly(A) tail (Chang et al., 2014, Mol. Cell 53(6): 1044-1052). However, as the poly(A) tail is not encoded in the respective DNA sequence, but enzymatically added to the transcribed pre-mature mRNA molecule, its length remains difficult to optimize.

Although the length of the poly(A) tail is known to be one of the most important physiological factors influencing mRNA stability and translational efficiency, existing technologies struggle with the production of mRNA molecules with defined poly(A) tail length on large scale. mRNA molecules for protein synthesis, e.g. in therapeutic applications, are primarily generated by in vitro transcription. Such approaches are based on DNA templates, in which the poly(A) tail is already encoded and which are amplified by cloning or polymerase chain reaction (PCR). Compared to an enzymatically catalyzed addition of a poly(A) tail to a generated mRNA these approaches theoretically have the advantage of providing poly(A) tails of defined and reproducible length (Holtkamp et al., 2006, Blood, 108(13), 4009-4018). In view of large scale production of mRNA molecules, plasmid based approaches are of special interest. Plasmid production is well established, can easily be scaled up and performed under Good Manufacturing Practice conditions. Compared to PCR based approaches, plasmid production costs and the risk of obtaining undesired mutations in coding sequences of the mRNA molecule are comparatively low. However, one main challenge persists using plasmids for bacterial amplification of template DNA sequences: homopolymeric sequences, such as the sequence encoding the poly(A) tail, can recombine during bacterial amplification of the plasmid DNA and, as a consequence, the sequences encoding the poly(A) tails are shortened over time in an unpredictable manner (Grier et al., 2016, Mol. Ther. Nucleic Acids, 5(4):e306). Grier and colleagues reported for example that sequences encoding a 70 nucleotide long poly(A) tail remained stable in contrast to sequences encoding poly(A) tails that consisted of at least 100 nucleotides, which is still much shorter than the on average 300 nucleotides long poly(A) tail of newly synthesized mature mRNA molecules in eukaryotes (Grier et al., 2016, Mol. Ther. Nucleic Acids, 5(4):e306). In an attempt to increase the poly(A) tail length, research focused on the use of a linear plasmid system, which allows stable cloning of sequences encoding poly(A) tails of up to 500 nucleotides (Grier et al., 2016, Mol. Ther. Nucleic Acids, 5(4):e306). In particular, a sequence encoding the mRNA molecule can be incorporated into a plasmid using a multiple cloning site (MCS). Using a unique site for a site-specific restriction enzyme, sequences encoding a comparatively short poly(A) tail can be added in an iterative process, thus allowing the expansion of the poly(A) tail encoding sequence comprised in the plasmid. However, it remains unclear how this system can efficiently be scaled up for large scale production of templates for in vitro transcribed mRNAs as the used linear plasmid is a low copy plasmid (BigEasy® v2.0 Linear Cloning System (pJAZZ® Vectors), Lucigen). Hence, there is still a need to have at hand alternative solutions for being able to deliver on large scale templates for in vitro transcription of mRNA molecules with defined and stable poly (A) tail length.

The present application addresses the need for in vitro transcription templates that encode mRNA molecules with defined poly(A) tail lengths and that exhibit a reduced recombination of the poly(A) tail encoding sequence during amplification in a bacterial cell by providing the embodiments as recited in the claims.

In particular, the present invention relates to a DNA plasmid comprising a DNA sequence which contains (i) a first nucleotide sequence which encodes an mRNA molecule and, located downstream thereof, (ii) a second nucleotide sequence which encodes a modified poly(A) tail, wherein said second nucleotide sequence is characterized in that it consists of (a) at least two A elements each defined as a nucleotide sequence consisting of 55 to 65 T nucleotides, and (b) at least one S element each S element consisting of (b1) one nucleotide that is not a T nucleotide, or (b2) 2 to 10 nucleotides, preferably 6 nucleotides, wherein each of the two terminal nucleotides is not a T nucleotide; wherein the total number of A elements is one more than the total number of S elements, and wherein any two A elements are separated by one S element. In other words, the present invention relates to a DNA plasmid comprising a DNA sequence that can be transcribed, preferably in vitro, into an mRNA molecule with a modified, i.e. segmented poly(A) tail.

It has surprisingly been found that a DNA plasmid comprising such a DNA sequence which encodes an mRNA molecule with a modified poly(A) tail shows reduced recombination during amplification of said DNA plasmid in a bacterial cell compared to the same DNA plasmid comprising a DNA sequence which encodes the same mRNA molecule with the same poly(A) tail, but without said S elements.

In the context of the present invention, the terms "DNA" and "RNA" refer to single- or double-stranded DNA or RNA molecules. If not stated otherwise, the terms "DNA" and "DNA molecule" refer to a double-stranded DNA molecule built up of A, C, G, and/or T nucleotides, and the terms "RNA" and "RNA molecule" refer to a single-stranded RNA molecule built up of A, C, G, and/or U nucleotides. Herein, said A, C, G, T, and U nucleotides refer to nucleotides comprising adenine, guanine, cytosine, thymine, and uracil as the respective nitrogenous base.

In the context of the present invention the term "DNA plasmid" refers to a plasmid consisting of a double-stranded DNA molecule. If not stated otherwise, the term "plasmid" refers to a circular DNA molecule, though the term can also encompass linear DNA molecules. In particular, the term "plasmid" also covers molecules which result from linearizing a circular plasmid by cutting it, e.g. with a restriction enzyme, thereby converting the circular plasmid molecule into a linear molecule. Plasmids can replicate, i.e. amplify in a cell independently from the genetic information stored as chromosomal DNA in the cell and can be used for cloning, i.e. for amplifying genetic information in a bacterial cell. Preferably, the DNA plasmid according to the present invention is a medium- or high-copy plasmid, more preferably a high-copy plasmid. Examples for such high-copy plasmids are vectors based on pUC, pBluescript®, pGEM®, pTZ plasmids or any other plasmids which contain an origin of replication (e.g. pMB1, pColE1) that support high copies of the plasmid.

The plasmid according to the present invention preferably comprises at least an origin of replication (ORI), a marker gene or a fragment thereof and/or a reporter gene or a fragment thereof, and unique restriction sites which allow for the insertion of DNA elements, preferably restriction sites in the form of a multiple cloning site (MCS). The ORI is essential for replication. A marker gene such as an antibiotics resistance gene is advantageous to identify cells containing a plasmid that comprises said marker gene. A reporter gene such as lacZ or luciferase is advantageous to measure the strength and/or regulation of expression of a target gene it is linked to or it can be used as a vicarious target gene for testing the expression and/or establishing a new approach or system. An MCS comprises several restriction sites that are unique within the DNA plasmid and that are each specifically recognized by a restriction enzyme. In particular, an MCS is advantageous for incorporating genetic elements such as the DNA sequence or the second nucleotide sequence according to the present invention into a suitable DNA plasmid, preferably a high-copy DNA plasmid. In case of the latter, the DNA plasmid further comprises a target gene (encoding an mRNA) to which the modified poly(A) encoded by the second nucleotide sequence is linked to.

A double-stranded DNA molecule such as a DNA plasmid consists of two complementary DNA strands. The term "complementary" refers to nucleotides, the nitrogenous bases of which can naturally bind to each other by hydrogen bonds, i.e. A and T nucleotides, A and U nucleotides as well as C and G nucleotides. According to the present invention, one of the two strands of a double stranded DNA molecule comprises a "DNA sequence". Herein, the term "DNA sequence" refers to a part of one strand of a double-stranded DNA molecule such as a DNA plasmid. According to the present invention said DNA sequence is built of A, C, G, and T nucleotides and comprises a first nucleotide sequence and a second nucleotide sequence as defined herein.

In the context of the present invention the "first nucleotide sequence" comprised in said DNA sequence is a "nucleotide sequence which encodes an mRNA molecule". In other words, said first nucleotide sequence refers to the part of said DNA sequence that can be used as a template during transcription, i.e. the synthesis of an mRNA molecule. Hence, in case an "mRNA molecule" is transcribed from the first nucleotide sequence, said mRNA has a nucleotide sequence that is complementary to said first nucleotide sequence except that instead of T nucleotides U nucleotides are used for synthesis of the mRNA molecule. As the poly(A) tail is naturally not encoded in the DNA sequence, but enzymatically added to the mRNA molecule during and/or after transcription, the term a "nucleotide sequence which encodes an mRNA molecule" refers to the part of said DNA sequence that can be used as a template during transcription of an mRNA molecule without any poly(A) tail.

Herein, "encoding" or "encode" refers to i) genetic information comprised in a DNA sequence that can be transcribed into an mRNA molecule, and/or ii) genetic information comprised in an mRNA molecule that can be translated into an amino acid sequence. Hence, these terms also cover genetic information comprised in the DNA that can be converted via transcription of an mRNA molecule into an amino acid sequence such as a protein.

Herein, the terms "mRNA molecule" and "mRNA" are used interchangeable and refer to a class of RNA molecules, preferably single-stranded sequences built up of A, C, G, and U nucleotides that contain one or more coding sequences. Said one or more coding sequence can be used as a template during synthesis of an amino acid sequence during translation. In other words, the term "mRNA" should be understood to mean any RNA molecule which is suitable for the expression of an amino acid sequence or which is translatable into an amino acid sequence such as a protein.

Further features of the first nucleotide sequence encoding an mRNA molecule and of the encoded mRNA molecule are described in further detail below.

According to the present invention, said first nucleotide sequence comprised in the DNA sequence contained in a DNA plasmid, is followed by a second nucleotide sequence comprised in said DNA sequence, i.e. said second nucleotide sequence is located downstream of said first nucleotide sequence. In other words, said two sequences are located on the same strand of a single- or double-stranded DNA molecule such that in case transcription takes place the first nucleotide sequence is transcribed first and then the second nucleotide sequence.

In particular, said two nucleotide sequences are located in close proximity to or directly linked to each other. In a preferred embodiment, the first nucleotide sequence and the second nucleotide sequence are directly linked to each other, i.e. there are no intervening nucleotides. However, it is also possible that the first and the second nucleotide sequence are separated by intervening nucleotides. Preferably, the first and the second nucleotide sequences are separated by not more than 100 nucleotides, more preferably not more than 50, 40, or 30 nucleotides, and most preferably by not more than 20, 10, or 5 nucleotides.

According to the present invention, the DNA sequence of the DNA plasmid comprises a first nucleotide sequence and, located downstream thereof, a second nucleotide sequence. Said "second nucleotide sequence" is a "nucleotide sequence which encodes a modified poly(A) tail". Herein, this refers to the part of said DNA sequence that can be used as a template for the synthesis of a modified poly(A) tail during transcription, preferably during in vitro transcription, of said DNA sequence. Naturally occurring poly(A) tails which are enzymatically added to a pre-mature mRNA molecule normally consist of A nucleotides. Such naturally occurring poly(A) tails are also referred to in the following as conventional poly(A) tails.

According to the present invention the term "modified poly(A) tail" refers to a segmented poly(A) tail that comprises nucleotides other than A nucleotides. In particular, said second nucleotide sequence encoding a modified poly (A) tail according to the present invention is characterized in that it consists of (a) at least two A elements each defined as a nucleotide sequence consisting of 35 to 65 T nucleotides, preferably of 55 to 65 T nucleotides, and (b) at least one S element each S element consisting of (b1) one nucleotide that is not a T nucleotide, or (b2) 2 to 10 nucleotides, preferably 6 nucleotides, wherein each of the two terminal nucleotides is not a T nucleotide; wherein the total number of A elements is one more than the total number of S elements, and wherein any two A elements are separated by one S element.

According to the present invention said A elements and said S elements are alternately disposed in said second nucleotide sequence. Hence, the term "wherein any two A elements are separated by one S element" is intended to be understood as "wherein any two consecutive A elements are separated by one S element". For illustration, in case of three A elements and two S elements the second sequence according to the present invention consists of one, i.e. the first, A element; one S element; another, i.e. the second, A element; another S element; and a further, i.e. the third, A element. Hence, in this example the term "any two A elements" refers to the first and the second A element as well as the second and the third A element, but not to the first and the third A element. Thus, this term refers to any of the at least two A elements and the closest A element of the remaining A elements.

In some embodiments, the DNA sequence according to the present invention comprises a first nucleotide sequence followed by a second nucleotide sequence followed by one or more additional nucleotides other than T nucleotides. Said additional nucleotides are preferably 1 to 5 C nucleotides, more preferably 1 C nucleotide. In other words, the DNA sequence can encode an mRNA molecule, a modified poly (A) tail, and additional nucleotides, preferably one G nucleotide.

As demonstrated by the appended Examples, it has been found that using a DNA plasmid comprising a DNA sequence which contains a first and a second nucleotide sequence that encode an mRNA molecule and a modified poly(A) tail according to the present invention results in a reduced recombination during amplification of said DNA plasmid in a bacterial cell compared to the same DNA plasmid but with a second nucleotide sequence which encodes an unmodified poly(A) tail consisting of the same total number of A nucleotides as encoded by the second nucleotide sequence according to the present invention. In other words, using a DNA plasmid according to the present invention results in a reduced recombination during amplification of said DNA plasmid in a bacterial cell compared to the same DNA plasmid but without said at least one S element between said at least two A elements.

Surprisingly, it has also been observed that, at the same time, the stability and the translational efficiency of the polyribonucleotide transcribed from the DNA sequence according to the present invention are generally not negatively affected by the modified poly(A) tail as defined above.

Herein, the term "recombination" refers to homologous recombination, in which nucleotide sequences are exchanged between two highly similar or identical nucleotide sequences comprised for example in DNA molecules such as DNA plasmids and/or chromosomes. The term "recombination" comprises intramolecular homologous recombination events, i.e. recombination of two highly similar or identical nucleotide sequences comprised in the same DNA molecule. In the context of the present invention this refers in particular to the recombination of a nucleotide sequence encoding a modified and a conventional poly(A) tail, respectively, and another highly similar or identical nucleotide sequence comprised in the same DNA plasmid during amplification of said plasmid, and/or to the recombination of the two terminal parts of such a nucleotide sequence. Alternatively or additionally, the term "recombination" comprises intermolecular homologous recombination events between a nucleotide sequence encoding a modified and a conventional poly(A) tail comprised in a DNA plasmid, respectively, and a highly similar or identical nucleotide sequence comprised in another DNA molecule, e.g. another DNA plasmid, comprised in the same cell for example.

According to the present invention, the term "reduced recombination" means that recombination is reduced by at least 5%, preferably by at least 10%, more preferably by at least 25%, even more preferably by at least 50%, and most preferably by 100%.

A reduction in recombination can be determined for example by the following procedure: genetically identical bacterial cells are used for amplifying a DNA plasmid according to the present invention (group I) and for amplification of the same DNA plasmid except that the second nucleotide sequence does not comprise said at least one S element (group II), respectively. Using routine lab procedures, bacterial cells can be lysed upon amplification, DNA plasmids obtained and linearized and the comprised DNA sequences or second nucleotide sequences purified. Obtained DNA sequences, especially obtained second nucleotide sequences can then be investigating qualitatively in view of nucleotide composition, sequence, and/or length for example by sequencing and/or electrophoresis such as gel or capillary electrophoresis. Alternatively or additionally, occurrence and frequency of recombination can be determined quantitatively by measuring the length of the second nucleotide sequences, calculating the ratio of second nucleotide sequences that have the expected length as defined by the originally used second nucleotide sequence and the total number of second nucleotide sequences within each group, and comparing the ratio obtained per group between groups. Alternatively, the extracted DNA sequences can be transcribed in vitro before investigating the length of the transcribed poly(A) tails within and between group I and II as described above in case of the second nucleotide sequences.

Such a reduction of recombination has been observed for DNA plasmids comprising a second nucleotide sequence according to the present invention. In particular, it has, e.g., been observed that S elements consisting of a single nucleotide are advantageous for reducing recombination during bacterial amplification. Thus, in a particularly preferred embodiment of the present invention, the DNA plasmid comprises a first nucleotide sequence encoding an mRNA molecule and a second nucleotide sequence encoding a modified poly(A) tail, wherein any one of said S elements consists of one C nucleotide or one A nucleotide, preferably of one C nucleotide.

In some embodiments the second nucleotide sequence according to the present invention consists of two A elements separated by one A nucleotide. More preferably, said two A elements are separated by one C nucleotide.

In some embodiments the second nucleotide sequence according to the present invention consists of three A elements, wherein any two A elements are separated by one A nucleotide. Preferably, any two of said three A elements are separated by one C nucleotide.

In some embodiments the second nucleotide sequence according to the present invention consists of four A elements, wherein any two A elements are separated by one A nucleotide. Preferably, any two of said four A elements are separated by one C nucleotide.

In some embodiments the second nucleotide sequence according to the present invention consists of five A elements, wherein any two A elements are separated by one A nucleotide. Preferably, any two of said five A elements are separated by one C nucleotide.

In some embodiments the second nucleotide sequence according to the present invention consists of six A elements, wherein any two A elements are separated by one A nucleotide each. Preferably, any two of said six A elements are separated by one C nucleotide.

In some embodiments the second nucleotide sequence according to the present invention consists of seven A elements, wherein any two A elements are separated by one A nucleotide. Preferably, any two of said seven A elements are separated by one C nucleotide.

In some embodiments the second nucleotide sequence according to the present invention consists of eight A elements, wherein any two A elements are separated by one A nucleotide. Preferably, any two of said eight A elements are separated by one C nucleotide.

In case more than one S element is comprised in the second nucleotide sequence said at least two S elements can have the same sequence or can vary in their sequence. Preferably, said at least two S elements each consist of i) the same nucleotide in case of one nucleotide, or ii) the same nucleotide sequence in case of 2 to 10 nucleotides, preferably 6 nucleotides.

Hence, in some embodiments each of the at least one S elements comprised in the second nucleotide sequence according to the present invention consists of an A nucleotide. Preferably, each of the at least one S elements comprised in the second nucleotide sequence according to the present invention consists of a C nucleotide.

In case of at least two S elements, in some embodiments at least one, but not all of the S elements can consist of an A nucleotide and each of the at least one remaining S elements can consist of i) one G or preferably of a C nucleotide, or of ii) 2 to 10 nucleotides, preferably 6 nucleotides, wherein each of the two terminal nucleotides is not a T nucleotide.

In case of at least two S elements, in some embodiments at least one, but not all of the S elements preferably consist of a G nucleotide and each of the at least one remaining S elements can consist of i) an A or a C nucleotide, or of ii) 2 to 10 nucleotides, preferably 6 nucleotides, wherein each of the two terminal nucleotides is not a T nucleotide.

In some embodiments the number of A elements comprised in the nucleotide sequence encoding a modified poly(A) tail contained in said DNA sequence of a DNA plasmid as defined above is two, three or four. In other words, in particularly preferred embodiments said second nucleotide sequence which encodes a modified poly(A) tail consists of i) two A elements flanking one S element, ii) three A elements in alternating order with two S elements, or iii) four A elements in alternating order with three S elements; with A and S elements as defined above.

In some embodiments said second nucleotide sequence which encodes a modified poly(A) tail consists of two A elements each consisting of the same number of T nucleotides in alternating order with one S element which consists of i) 6 nucleotides wherein each of the two terminal nucleotides is not a T nucleotide or preferably ii) a C nucleotide.

In some embodiments said second nucleotide sequence which encodes a modified poly(A) tail consists of three A elements each consisting of the same number of T nucleotides in alternating order with two S elements, wherein all of said two S elements each consist of i) 6 nucleotides wherein each of the two terminal nucleotides is not a T nucleotide or preferably ii) a C nucleotide.

In some embodiments said second nucleotide sequence which encodes a modified poly(A) tail consists of four A elements each consisting of the same number of T nucleotides in alternating order with three S elements, wherein all of said three S elements each consist of i) 6 nucleotides wherein each of the two terminal nucleotides is not a T nucleotide or preferably ii) a C nucleotide.

In some embodiments said second nucleotide sequence which encodes a modified poly(A) tail consists of two, three, or four A elements, wherein at least two of said A elements differ in their number of T nucleotides, in alternating order with one, two, or three S elements, respectively, wherein all of said S elements each consist of i) 6 nucleotides wherein each of the two terminal nucleotides is not a T nucleotide.

In some embodiments said second nucleotide sequence which encodes a modified poly(A) tail consists of two, three, or four A elements, wherein at least two of said A elements differ in their number of T nucleotides, in alternating order with one, two, or three S elements, respectively, wherein preferably all of said S elements each consist one C nucleotide.

In some embodiments of the DNA plasmid as defined above, the number of A elements is four and the nucleotide sequences of the four A elements together have an overall length of 240 nucleotides.

Preferably, each A element has a length of 60 nucleotides. In other words, in particularly preferred embodiments said second nucleotide sequence which encodes a modified poly (A) tail consists of four A elements in alternating order with three S elements, wherein the four A elements together consist of 240 nucleotides and preferably have the same length each.

More preferably, said second nucleotide sequence which encodes a modified poly(A) tail consists of four A elements each consisting of 60 T nucleotides in alternating order with three S elements, wherein all three S elements each consist of i) 6 nucleotides wherein each of the two terminal nucleotides is not a T nucleotide or preferably ii) one C nucleotide.

In some embodiments of the DNA plasmid as defined above, the number of A elements is two and the nucleotide sequences of the two A elements together have an overall length of 120 nucleotides.

Preferably, each A element has a length of 60 nucleotides. In other words, in particularly preferred embodiments said second nucleotide sequence which encodes a modified poly (A) tail consists of two A elements having together a total length of 120 nucleotides. In other words, in particularly preferred embodiments said second nucleotide sequence which encodes a modified poly(A) tail consists of two A elements in alternating order with one S element, wherein the two A elements together consist of 120 nucleotides and preferably have the same length each. More preferably, said second nucleotide sequence which encodes a modified poly (A) tail consists of two A elements each consisting of 60 T nucleotides flanking one S element consisting of i) 6 nucleotides wherein each of the two terminal nucleotides is not a T nucleotide or preferably ii) one C nucleotide.

In some embodiments of the DNA plasmid as defined above, said DNA plasmid contains in the nucleotide sequence encoding a modified poly(A) tail three A elements having together a total length of 120 nucleotides. In other words, in this embodiment of the DNA plasmid as defined above, the number of A elements is three and said nucleotide sequences of the three A elements together have an overall length of 120 nucleotides, preferably each A element having a length of 40 nucleotides. Hence, the second nucleotide sequence encoding said modified poly(A) tail can consist of three A elements alternating ordered with two S elements. Preferably, each of the three A elements consists of 40 T nucleotides and each of the two S elements of i) preferably one C nucleotide or ii) 6 nucleotides wherein each of the two terminal nucleotides is not a T nucleotide.

According to the present invention, the DNA plasmid comprises a DNA sequence comprising a first nucleotide sequence followed by a second nucleotide sequence as defined above. Preferably, the first nucleotide sequence is preceded by a promoter comprised in the DNA sequence or the DNA plasmid. The promoter is involved in controlling and initiating the transcription of the following nucleotide sequence such as the DNA sequence comprising the first nucleotide sequence or the first nucleotide sequence. Hence, a promoter comprised in the DNA plasmid, preferably a strong promoter, can be advantageous for comparing effects of other genetic elements on the transcription duration and/or intensity of the following nucleotide sequence encoding an mRNA molecule. On the other hand, a promoter comprised in the DNA sequence, preferably a strong promoter, can be advantageous for optimizing transcription duration and/or intensity of the following nucleotide sequence encoding an mRNA molecule.

The promoter comprises at least a recognition site followed by a binding site. Recognition and binding site can interact with amino acid sequences that mediate or regulate transcription. The binding site is located closer to the first nucleotide sequence comprised in the DNA sequence according to the invention compared to the recognition site. For example, the recognition site can be a −35 box and the binding site a −10 box located in a distance of approximately 35 nucleotides and 10 nucleotides before the transcription start site, respectively. The binding site can be for example a Pribnow box in prokaryotes and a TATA box in eukaryotes. Preferably the binding site is a Pribnow box comprised in the DNA plasmid or the DNA sequence close to the first nucleotide sequence.

Optionally, the promoter comprises at least one additional regulatory element such as an AT-rich upstream element located approximately 40 and/or 60 nucleotides before the transcription start site, and/or additional regulatory elements located between the recognition and the binding site that enhance the activity of the promoter.

In a particularly preferred embodiment, the promoter is a strong promoter. In other words, the promoter comprises sequences that promote transcription of the following DNA sequence according to the present invention. Strong promoters are known to the person skilled in the art, for example the RecA promoter derived OXB18, OXB19, and OXB20 promoters for *Escherichia coli*, or can be identified or synthesized by routine lab procedures.

Optionally, the promoter is preceded by additional regulatory elements such as enhancers comprised in the DNA plasmid that promote transcription of the DNA sequence according to the present invention.

The DNA sequence comprises a first nucleotide sequence which encodes an mRNA molecule, i.e. can be converted into an mRNA molecule during transcription, wherein synthesis of the mRNA molecule starts with its 5' end and ends with its 3' end. Features of the first nucleotide sequence encoding an mRNA molecule are described in more detail below in connection with the encoded mRNA molecule.

The first nucleotide sequence comprises at least one region that encodes an untranslated region (UTR) and at least one coding region. Preferably, the first nucleotide sequence encodes at least the 5' UTR and the coding region of the encoded mRNA molecule. The coding region can comprise non-coding and coding parts. Preferably, the coding region consists of at least one coding part that encodes the part of the mRNA molecule that can be translated into an amino acid sequence, or parts thereof.

In a particularly preferred embodiment, the first nucleotide sequence comprises a region encoding a 5' UTR followed by a coding region followed by a region encoding a 3' UTR of the encoded mRNA molecule.

According to the present invention, the first nucleotide sequence encodes an mRNA molecule. Preferably, the first nucleotide sequence encodes an mRNA comprising a 5' UTR, a coding sequence and a 3' UTR.

The 5' end of the 5' UTR is defined by the transcriptional start site and its 3' end is followed by the coding sequence. The coding sequence is terminated by the start and the stop codon, i.e. the first and the last three nucleotides of the mRNA molecule that can be translated, respectively. The 3' UTR starts after the stop codon of the coding sequence and is followed by the modified poly(A) tail encoded by the second nucleotide sequence according to the present invention.

The 5' UTR generally comprises at least one ribosomal binding site (RBS) such as the Shine-Dalgarno sequence in prokaryotes and the Kozak sequence or translation initiation site in eukaryotes. RBS promote efficient and accurate translation of an mRNA molecule by recruiting ribosomes during initiation of translation. The activity of a given RBS can be optimized by varying its length and sequence as well as its distance to the start codon. Alternatively or optionally, the 5' UTR comprises internal ribosome entry sites or IRES.

In some embodiments, the mRNA molecule comprises a 5' UTR that comprises additionally one or more additional regulatory sequences such as a binding site for an amino acid sequence that enhances the stability of the mRNA molecule, a binding site for an amino acid sequence that enhances the translation of the mRNA molecule, a regulatory element such as a riboswitch, a binding site for a regulatory RNA molecule such as an miRNA molecule, and/or a nucleotide sequence that positively affects initiation of translation. Furthermore, within the 5' UTR there are preferably no functional upstream open reading frames, out-of-frame upstream translation initiation sites, out-of-frame upstream start codons and/or nucleotide sequences giving rise to a secondary structure that reduces or prevents translation. The presence of such nucleotide sequences in the 5' UTR can have a negative effect on translation.

The coding sequence is encoded by the at least one coding part of the first nucleotide sequence and comprises codons that can be translated into an amino acid sequence. Further features of the encoded amino acid sequence are described in detail below.

The coding sequence can contain the codons of a naturally occurring coding sequence or it can be a partially or completely synthetic coding sequence. Alternatively, the coding sequence can be a partly or fully codon optimized sequence derived from the natural sequence to be used. Most of the amino acids are encoded by more than one codon, i.e. three consecutive nucleotides of an mRNA molecule that can be translated into an amino acid. Codons exist that are used preferentially in some species for a given amino acid. The presence of more often occurring codons can enhance the amount of amino acid sequences translated based on a given mRNA molecule compared to the same mRNA molecule but comprising comparably rare codons. Hence, it is advantageous to species specific adapt the codons in a given coding sequence by avoiding rare codons and enhancing the occurrence of abundant codons for a given amino acid to improve the translation of said mRNA.

The mRNA may optionally also comprise a 3' UTR. The 3' UTR may comprise one or more regulatory sequences such as a binding site for an amino acid sequence that enhances the stability of the mRNA molecule, a binding site for a regulatory RNA molecule such as a miRNA molecule, and/or a signal sequence involved in intracellular transport of the mRNA molecule.

In a particularly preferred embodiment, the mRNA molecule encoded by the first nucleotide sequence comprises a 5' UTR with at least one RBS and/or IRES, a coding sequence with optimized codons and a 3' UTR with at least one regulatory sequence as defined above.

The mRNA molecule according to the present invention comprises a coding sequence, i.e. a sequence encoding an amino acid sequence. As regards the function of the encoded amino acid sequence, there is no limitation and possible amino acid sequences to be encoded by said polyribonucleotide are described further below. Herein, the term "amino acid sequence" encompasses any kind of amino acid sequence, i.e. chains of two or more amino acids which are each linked via peptide bonds and refers to any amino acid sequence of interest. Preferably, the encoded amino acid sequence is at least 5 amino acids long, more preferably at least 10 amino acids, even more preferably at least 50, 100, 200 or 500 amino acids. In other words, the term "amino acid sequence" covers short peptides, oligopeptides, polypeptides, fusion proteins, proteins as well as fragments thereof, such as parts of known proteins, preferably functional parts. These can, for example be biologically active parts of a protein or antigenic parts such as epitopes which can be effective in raising antibodies.

Preferably, the function of the encoded amino acid sequence in the cell or in the vicinity of the cell is needed or beneficial, e.g. an amino acid sequence the lack or defective form of which is a trigger for a disease or an illness, the provision of which can moderate or prevent a disease or an illness, or an amino acid sequence which can promote a process which is beneficial for the body, in a cell or its vicinity. The encoded amino acid sequence can be the complete amino acid sequence or a functional variant thereof. Further, the encoded amino acid sequence can act as a factor, inducer, regulator, stimulator or enzyme, or a functional fragment thereof, where this amino acid sequence is one whose function is necessary in order to remedy a disorder, in particular a metabolic disorder or in order to initiate processes in vivo such as the formation of new blood vessels, tissues, etc. Here, functional variant is understood to mean a fragment which in the cell can undertake the function of the amino acid sequence whose function in the cell is needed or the lack or defective form whereof is pathogenic.

Preferably, such an amino acid sequence is advantageous with respect to applications in supplemental or medical purposes to generate or regenerate physiological functions caused by suboptimal amino acid sequence biosynthesis and thus also to favorably influence directly or indirectly the course of diseases. Disorders with known genetic base are for example cystic fibrosis, haemophilia, hypertension, elevated cholesterol level, cancer, neurodegenerative disorders, mental illness and others. An online catalogue with presently 22,993 entries of Human Genes and Genetic Disorders together with their respective genes and a description of their phenotypes are available at the ONIM (Online Mendelian Inheritance in Man) webpage (http://onim.org); sequences of each are available from the Uniprot database (http://www.uniprot.org). As non-limiting examples, the following Table 1 lists some congenital diseases, and the corresponding gene(s). Due to the high degree of interaction of cellular signalling pathways, the mutation of a certain gene causes a multiply of pathogenic symptoms, of which only a characteristic one is listed in Table 1.

TABLE 1

| Disease | Pathology | Gene, heredity |
|---|---|---|
| | Blood diseases | |
| Fanconi Anemia | Anemia and neutropenia, evidence that a DNA repair mechanism is affected | FANCA, autosomal recessive |
| Hemophilia-A | Abnormal bleeding | Coagulation Factor VIII, X-chromosomal recessive |
| Hemophilia-B | Abnormal bleeding | Coagulation Factor IX, X-chromosomal recessive |
| Hereditary Spherocytosis (various types) | spherical-shaped erythrocytes (spherocytes) | Ankyrin (ANK1) |
| Paroxysmal nocturnal hemoglobinuria | Anemia and presence of blood in the urine | PIG-A, X-chromosomal |
| Porphyria cutanea tarda | Overproduction of heme, iron overload | Uroporphyrinogen decarboxylase (UROD), autosomal recessive |
| Severe combined immune deficiency (SCID) | Due to impaired DNA synthesis severe immune deficiency in humoral and cellular immunity | Adenosine deaminase, autosomal recessive, IL-2R-γ, JAK3, (IL-7R-α, RAG1/2, Artemis, CD3δ, CD3ε |
| Sickle-cell anemia | Abnormal hemoglobin (HbS) | β-Hemoglobin (HB), autosomal recessive |
| Thalassemia (α- and β form) | Lack of α- or β hemoglobin resulting in anemia | Deletion of HBA1 and/or HBA2, |
| Von Willebrand disease (three types known, Type-III is most severe) | Abnormal bleeding, hemorrhage similar to hemophilia A and B | Autosomal dominant and recessive forms |
| | Cancer | |
| Malignant melanoma | P16 mutation leads to uncontrolled proliferation of fibroblasts | Cyclie dependant kinase inhibitor 2 (CDKN2) |
| Neurofibromatosis (2 types) | Benign tumors on auditory nerves leads to deafness | NF1, NF2, autosomal dominant |
| | Deafness (Ear) | |
| Deafness | Hearing loss | Deafness-1A (DFNB1), autosomal recessive |
| Pendred syndrome | Hearing loss | Pendrin (PDS), autosomal recessive |
| | Heart | |
| Ataxia telangiectasia | DNA damage repair disturbed, | ATM, |
| Atherosclerosis | Increase of blood cholesterol | apoE, |
| LQT Syndrome (Long QT) | Potassium channel defect | LQT1 and other genes |
| Von-Hippel Lindau Syndrome | Abnormal growth of blood vessels, can lead to cancer | VHL, autosomal dominant |
| William's Beuren Syndrome | Deletion of elastin results in vascular defects, supravalvular aortic stenosis | Deletion of elastin and LIM kinase genes |
| | Metabolic disorders and glycogen storage diseases | |
| Adrenoleukodystrophy | Disturbed fatty acid transport and metabolism | ABCD1, X-chromosomal |
| Alkaptonuria | Nitrogen metabolism defect, Urine turns dark when exposed to oxygen | Homogentisic Oxidase, autosomal recessive |
| Diabetes type I | Disturbed insulin production | IDDM1, IDDM2, GCK, . . . |
| Galactosemia | disorder of galactose metabolism | Galactose-1-phosphate uridyltransferase gene (GALT), autosomal recessive |

TABLE 1-continued

| Disease | Pathology | Gene, heredity |
|---|---|---|
| Gauche disease | Disturbance of fat metabolism | Glucocerebrosidase |
| Glucose Galactosidase Malabsorption | Disturbed glucose and galactose transport out of the intestinal lumen resulting in diarrhea | SGLT1, autosomal recessive |
| Glycogen storage diseaseType I, Von-Gierke's disease | Accumulation of glucose in liver and kidney | Glucose-6-Phosphatase, autosomal recessive |
| Glycogen storage disease Type II, Pompe's disease | Accumulation of glycogen in liver, heart, skeletal muscle, cardiomegaly | α-1-Glucosidase, autosomal recessive |
| Glycogen storage disease Type III, Cori's disease | Accumulation of glycogen in liver, heart, skeletal muscle, hepatoomegaly | Debranching enzyme, autosomal recessive |
| Glycogen storage disease Type V, McArdle's disease | Cannot untilize glycogen in muscle cells | Muscle phosphorylase, autosomal recessive |
| Glucose-6-Phosphate Dehydrogenase | Inability to maintain, glutathione leads to hemolytic anemia | G6PD X-chromosomal recessive |
| Hereditary Hemochromatosis (4 types) | Excess of iron in the body (esp. liver) due to excessive iron absorption in the gut | Hemochromatosis (HFE) |
| Homocystinuria | Nitrogen metabolism defect | Cystathione synthetase defect, autosomal recessive |
| Lesh Nyhan Syndrome | Accumulation of uric acid leading to gout, ureate stones and muscle loss | HPRT1, X-chromosomal |
| Maple Syrup Urine Disease | Amino acid metabolism defect leads to the accumulation of α-Ketoacides and death in the first months if untreated | Branched-chain-alpha-dehydrogenase (BCKDH) |
| Menkes' Syndrome | Reduced ability to absorb copper, leads to death in infancy if untreated | ATP7A, X-chromosomal recessive |
| Obesity | Elevated body weight | Polygenic, elevated leptin levels may play a role |
| Phenylketonuria | Inability to break down Phenylalanine into tyrosine leads to mental retardation | Phenylalanine hydroxylase (PAH), autosomal recessive |
| Tangier disease | reduced levels of plasma high density lipoproteins | ATP-binding cassette-1 gene (ABCA1) |
| Zellweger Syndrome (leads to death in infants) | High levels of iron and copper in the blood | PXR1 (receptor on the surface of peroxisomes) |
| Wilsons Disease | Copper accumulation in brain and liver | ATP7B (P-type ATPase), autosomal recessive |
| | Musculoskeletal system | |
| Achondroplasis | Short stature with a large head due to slow proliferation of chondrocytes | Fibroblast growth factor receptor 3 (FGF3R), |
| Charcot-Marie-Tooth Syndrome and its more severe form Dejerine-Sottas Syndrome | Degeneration of the muscles in limbs | Different forms caused by different gene mutations, autosomal recessive and X-chromosomal |
| Cockayne syndrome (2 types) | Premature aging and short stature, loss of "on the fly" DNA repair | group 8 excision repair cross-complementing protein (ERCC8) |
| Chondroectodermal dysplasia | Malformation of bones and polydactyly | EVC, autosomal recessive |
| Diastrophic dysplasia (DTD) | Malformed hands, sulfate transporter defect | DTDST gene |
| Duchenne muscular dystrophy | Enlargement of muscle tissue with subsequent loss function | DMD, X-chromosomal of recessive |
| Fibrodysplasia Ossificans Progressiva | Heterotopic bone formation | NOG, BMP, Autosomal dominant |
| Friedreich's ataxia | Heart enlargement and progressive loss of muscular coordination | Frataxin, autosomal recessive |

TABLE 1-continued

| Disease | Pathology | Gene, heredity |
|---|---|---|
| Hypophosphatasia | Production of an abnormal version of alkaline phosphatase affecting the mineralization process | ALPL, autosomal recessive |
| Marfan Syndrome | Connective tissue disorder due fibrillin deficiency | Fibrillin 1 (FBN), autosomal dominant |
| Myotonic dystrophy (onset during young adulthood) | Protein kinase defect in skeletal muscle cells | Dystrophia myotonica protein kinase (DMPK), autosomal dominant |
| Osteogenesis imperfect (various types) | Defect in type-I collagen formation leads to multiple fractures after birth | COL1A1, COL1A2 |
| Prader-Willi Syndrome | Decreased muscle tone and mental retardation | SNRPN (small ribonucleoprotein N) deleted due to a deletion on chromosome 15 |
| | Neurons and Brain | |
| Alzheimer disease | Increased amyloid production, progressive inability to remember facts | Polygenic, PS1, PS2, . . . |
| Amyotrophic lateral sclerosis (ALS) (various forms) | Progressive degeneration of motor neuron cells (defect in elimination superoxide radicals) | Superoxide dismutase 1 (SOD1), various genes involved |
| Angelman syndrome | Mental retardation with inadequate laughing | Genomic imprinting on chromosome 15 |
| Pyruvat dehydrogenase | Neurological defects if untreated | Pyruvat dehydrogenase, autosomal recessive |
| Refsum disease | Accumulation of phytanic acid leads to peripheral neuropathy | Phytanoyl-CoA hydroxylase (PHYH), autosomal recessive |
| Rett's syndrome | Mental retardation with arrested development between 6 and 18 months of age | Methyl-CpG-binding protein-2 (MECP2), X-chromosomal dominant |
| Tay-Sachs disease (various forms of severity) | Disturbed break down of GM2 ganglioside leads to neurological damage | HEXA(β-hexosaminidase A), autosomal recessive |
| LaFora Disease | Aggressive form of epilepsy | EPM2A, autosomal recessive |
| Essential tremor (variable forms) | Uncontrollable shaking | ETM1, ETM2, autosomal dominant |
| Fragile X syndrome | Lack of FMR1 RNA binding protein, mental retardation | FMR1 gene is not expressed due to an CGG amplification in the 5'UTR region |
| Huntington's disease | Progressive dementia with onset in adulthood | HTT (huntington), autosomal dominant |
| | Intestine | |
| Bartter's syndrome (3 types) | Renal disease | Kidney chloride channel B gene (CLCNKB), autosomal recessive |
| Polycystic kidney disease (2 types) | renal disease | PDK1, PDK2, autosomal dominant, there is also an autosomal recessive form known (ARPKD) |
| | Lung | |
| Alpha-1-antitrypsin | Defect alveoli due to uncontrolled release of elastase | SERPINA1, autosomal codominant |
| Asthma | Chronic inflammatory disorder of the airways | Polygenic |
| Cystic fibrosis | Excessively viscous mucous due to defective $Cl^-$ ion transport | CFTR (cystic fibrosis conductance transmembrane regulator), autosomal recessive |
| Surfactant metabolism dysfunction (various types) | Newborns are of normal body weight, but all fail to inflate | ATP-binding cassette transporter (ABCA3) |
| Primary ciliary dyskinesia | Excessively viscous mucous due to defective/missing cilia function | DNAI1, CCNO, CCDC40 among others |

TABLE 1-continued

| Disease | Pathology | Gene, heredity |
|---|---|---|
| Lysosomal storage diseases | | |
| Fabry's disease | Beyond others, skin lesions due to the accumulation of ceramide trihexoside | α-Galactosidase A, X-chromosomal recessive |
| Gaucher's Disease Type-I: adult form (normal lifespan under treatment) Type-II: infantile form (death before age 1) Type-Ill: juvenile form (onset in early childhood, less severe than Type-II) | Accumulation of glucocerebrosides (gangliosides, sphingolipids) | Glucocerebrosidase, autosomal recessive, |
| Hunter's Syndrome | Accumulation of mucopolysaccharides | L-iduronosulfat sulfatase, X-chromosomal recessive |
| Hurler's Syndrome (death by age of 10) | Accumulation of mucopolysaccharides | α-L-iduronidase, autosomal recessive |
| Niemann-Pick Disease (three distinct forms A, B, C) | Defect in releasing Cholesterol from lysosomes, accumulation of Sphingomyelin | Sphingomyelinase, autosomal recessive |
| Tay-Sachs disease (death by age of 4) | Accumulation of $G_{M2}$ ganglioside in neuronal cells | Hexosaminidase A, autosomal recessive |
| Skin | | |
| Albinism | Nitrogen metabolism defect | Tyrosinase deficiency, autosomal recessive |
| Albinism, oculocutaneous, type II | Reduced biosynthesis of melanin pigment | OCA2, autosomal recessive |
| Ehlers-Danlos Syndrome (various types) | Diaphragmatic hernia. common, retinal detachment | Various defects in collagen synthesis |
| Epidermolysis bullosa (various types including EB simplex, Junctional EB, Dystrophic EB and Kindler syndrome) | Defects in maintenance of keratinocyte structural stability or adhesion of the keratinocyte to the underlying dermis | Epidermolysis bullosa macular type (EBM), Epidermolysis bullosa 3 progressiva (EBR3), Epidermolysis bullosa 4 pseudojunctual (EBR4), Desmoplakin (DSP), Plakophilin-1 (PKP1), kreatin (KRT5, KRT14), plectin (PLEC), ITGA6, integrin subunit (ITGB4), laminin subunits (LAMA3, LAMP3, LAMB3, LAMC2), collagen (COL17A1 , COL7A1 (autosomal dominant), FERMT1, autosomal recessive |
| Hartnup's disease | Defect in tryptophan uptake in the gastrointestinal tract, light-sensitive skin | SLC6A19, autosomal recessive |
| Hereditary Hemorrhagic Telangiectasia, Osler-Weber-Rendu Syndrome | Telangiectasia of the skin and mucous membranes | Endoglin (ENG), autosomal dominant |
| Hypercholesterolemia, familial | elevation of serum cholesterol bound to low density lipoprotein, accumulation in skin and arteriosclerosis | Low-density lipoprotein receptor (LDLR), apolipoprotein B (APOB), autosomal dominant |
| Xeroderma pigmentosa | skin defect and melanoma due to UV exposure | DNA repair defect, autosomal recessive |
| Male pattern baldness | Disturbed conversion of testosterone into dihydrotestosterone in the skin | 5-α-reductase |

TABLE 1-continued

| Disease | Pathology | Gene, heredity |
|---|---|---|
| | Genetic liver diseases | |
| Amino acid metabolism disorders | Disruptions in the multistep process that breaks down the amino acid tyrosine and phenylalanine | FAH, TAT, HPD, autosomal recessive |
| Beta-thalassemia intermedia | Shortage of mature red blood cells | HBB, autosomal recessive |
| Crigler-Najjar syndrome | Deficiency in glucuronidation in which bilirubin gets dissolvable in water | UGT1A1, autosomal recessive |
| Fatty acid oxidation disorders | Deficiency in processing of long-chain fatty acids and very long-chain fatty acids resulting in lethargy and hypoglycemia | HADHA, ACADVL autosomal recessive |
| Fructose metabolism disorders | Impaired gluconeogenesis causing hypoglycemia | FBP1, ALDOB, autosomal recessive |
| Galactosemia | Deficiency in processing galactose | GALT, GALK1, GALE, autosomal recessive |
| Glycogen storage diseases | Disturbed breackdown of glucose 6-phosphate and glycogen leads to accumulation of glycogen as well as abnormal glycogen molecules causing cell damage | G6PC, SLC37A4, AGL, GBE1, autosomal recessive |
| Heme biosynthesis disorder | Decrease of uroporphyrinogen decarboxylase resulting in accumulation of compounds called porphyrins causing toxic levels in liver | UROD autosomal dominant, ALAS2 X-linked dominant, ALAD autosomal recessive |
| Lipid metabolism (transport) disorders | Shortage of functional protein, which prevents movement cholesterol and other lipids, leading to their accumulation in cells | NPC1, NPC2 of autosomal recessive, LDLR, autosomal dominant |
| Metal metabolism disorders | Disorders in the storage and transport of iron and copper resulting in accumulation in tissues and organs | ATP7B, HAMP, HFE, HFE2, autosomal recessive |
| Organic acid disorders (Acidurias/ Acidemias) | Disrupted break down of several protein building blocks (amino acids), certain lipids, and cholesterol | BCKDHA, BCKDHB, and DBT, PCCA and PCCB, MUT, MMAA, MMAB, MMADHC, MCEE, IVD, MCCC1 or MCCC2, autosomal recessive |
| Primary hyperoxaluria type 1 | Disrupted breakdown of glyoxylate leading to renal damage | AGXT, GRHPR, autosomal recessive |
| Progressive familial intrahepatic cholestasis | Buildup of bile acids in liver cells causing liver damage | ATP8B1, autosomal recessive |
| Thrombocyte activity disorder | Lack of enzyme activity disrupts the usual balance between bleeding and clotting | ADAMTS13, autosomal recessive |
| Urea cycle disorders | Disorder of the urea cycle which causes a form of hyperammonemia | OTC (X-linked disorder), CPS1, ASS1 and SLC25A13, ASL, autosomal recessive |

The protein encoded by the polyribonucleotide according to the present invention can also have the potential to induce an immunogenic reaction acting, e.g., as an antigen. Thus, polyribonucleotides according to the invention lend themselves to applications in supplemental or medical purposes including vaccination.

Suitable nucleotide sequences of the genetic elements described above such as UTRs, regulatory sequences and binding sites are nucleotide sequences that enhance the action and/or duration of action of the mRNA molecule. Such nucleotide sequences as well as coding regions and/or coding sequences as described above can be naturally occurring, mutagenized, or synthesized nucleotide sequences or a combination thereof and can be identified and adapted by routine experiments known to the person skilled in the art.

The present invention further relates to a bacterial host cell comprising the DNA plasmid as described above. The DNA plasmid according to the present invention can be stored and/or amplified in a bacterial host cell that is competent for transformation. Competent host cells are cells that have the ability to take up free, extracellular genetic material such as a DNA plasmid independent of its sequence. Naturally competent bacteria have the ability to bind extracellular genetic material using for example receptor proteins or protein complexes. Moreover, said cells have the ability to transfer genetic material from the extracellular space into the cell using for example peptides, proteins or protein complexes such as a DNA translocase. A wide range of bacterial cells known to the person skilled in the art is naturally capable of taking up exogenous DNA from the environment and can thus act as a bacterial host cell according to the present invention. Furthermore, competent bacterial host cells can be obtained from naturally non-competent bacterial cells using for example electroporation or chemicals such as a treatment with calcium ions accompanied with the exposure to elevated temperature. Upon uptake, the DNA plasmid is preferably neither degraded nor integrated in the bacterial host cell's genomic information.

Bacterial host cells include *Escherichia coli* (*E. coli*) cells which are well-known to the person skilled in the art. In *E. coli* cells, integration of extracellular genetic material into the host cell's genetic material can take place in a RecA-dependent process, i.e. a process that is dependent on the RecA protein. This protein is essential for repair and maintenance of DNA and involved in homologous recombination. Hence, in some embodiments the bacterial host cell according to the present invention is an *E. coli* cell, preferably an *E. coli* $recA^-$ cell. This might be advantageous to avoid integration of the genetic information comprised in the DNA plasmid according to the present invention into the *E. coli* cell's original genetic material.

The present invention further relates to the use of a nucleotide sequence which encodes a modified poly(A) tail as defined above for preparing a DNA plasmid showing reduced recombination during amplification in a bacterial host cell, wherein said nucleotide sequence is located downstream of a nucleotide sequence which encodes an mRNA molecule.

The DNA plasmid according of the present invention can be prepared by methods known to the person skilled in the art. Preferably, an MCS comprised in the DNA plasmid is cut, using a site specific restriction enzyme and the generated DNA plasmid ends are ligated to the ends of the DNA sequence. Thus, the DNA sequence according to the present invention is preferably terminated at both sites by said MCS.

As regards the nucleotide sequence which encodes a modified poly(A) tail, the nucleotide sequence which encodes an mRNA molecule, the DNA plasmid, and the reduction of recombination during amplification of said DNA plasmid in a bacterial host cell the same applies as it has been described above in connection with the DNA plasmid and the DNA sequence according to the invention. Moreover, also the other features of such a DNA plasmid and DNA sequence can be as described above.

The present invention further relates to the use of a nucleotide sequence which encodes a modified poly(A) tail as defined above for reducing recombination during amplification of a DNA plasmid in a bacterial host cell. In other words, a nucleotide sequence encoding a modified poly(A) tail as defined above can be used to reduce recombination during amplification of a DNA plasmid containing this nucleotide sequence in a bacterial cell compared to the same DNA plasmid but with a sequence encoding a conventional poly(A) tail, in particular in comparison to the same DNA plasmid in which the nucleotide sequence encoding a poly (A) tail does not contain any S elements. The DNA plasmid is preferably a plasmid which contains a nucleotide sequence encoding an mRNA molecule, wherein the nucleotide sequence encoding the modified poly(A) tail is placed downstream of the nucleotide sequence encoding the mRNA molecule. It is particularly advantageous to reduce recombination of the plasmid by replacing a nucleotide sequence encoding a conventional poly(A) tail by a nucleotide sequence encoding a modified poly(A) tail as defined above.

As regards the nucleotide sequence which encodes a modified poly(A) tail, the nucleotide sequence which encodes an mRNA molecule, the DNA plasmid, and the reduction of recombination during amplification of said DNA plasmid in a bacterial host cell the same applies as it has been described above in connection with the DNA plasmid according to the invention. Moreover, also the other features of such a DNA plasmid can be as described above.

The present invention further relates to a method for reducing recombination of a DNA plasmid comprising a DNA sequence which encodes an mRNA molecule and, located downstream thereof, a poly(A) tail, during amplification in a bacterial host cell, wherein said reduction is achieved by replacing the part of the DNA sequence which encodes the poly(A) tail by a nucleotide sequence which encodes a modified poly(A) tail as defined above.

Replacing a part of the DNA sequence can be performed for example using an MCS flanking said part of the DNA sequence and the nucleotide sequence that is used for replacement. Hence, the DNA plasmid can be cut using restriction enzymes at said MCS and the obtained fragments investigated using for example capillary or gel electrophoresis. Using said MCS, the part of the DNA plasmid not containing the part of the DNA sequence which encodes the poly(A) tail and the nucleotide sequence which encodes a modified poly(A) tail can then be ligated.

As regards the nucleotide sequence which encodes a modified poly(A) tail, the nucleotide sequence which encodes an mRNA molecule, the DNA plasmid, the bacterial host cell, and the reduction of recombination during amplification of said DNA plasmid in a bacterial host cell the same applies as it has been described above in connection with the DNA plasmid according to the invention. Moreover, also the other features of such a DNA plasmid can be as described above.

The present invention further relates to a method of producing a polyribonucleotide comprising a sequence encoding an amino acid sequence and a modified poly(A) tail as encoded by the nucleotide sequence as defined above, said method comprising the step of producing said polyribonucleotide by in vitro transcription from a DNA plasmid according to the invention.

Herein, the term "polyribonucleotide" refers to a single-stranded RNA molecule. The polyribonucleotide according to the present invention comprises the mRNA molecule encoded by the first nucleotide sequence and the modified poly(A) tail encoded by the second nucleotide sequence. In other words, the polyribonucleotide comprises a 5' UTR, a coding sequence, optionally a 3' UTR, and a modified poly(A) tail. In a particularly preferred embodiment, the polyribonucleotide comprises a 5' UTR with at least one RBS and/or IRES, a coding sequence with optimized codons, optionally a 3' UTR with at least one regulatory sequence, and a modified poly(A) tail. Optionally, the polyribonucleotide comprises additional nucleotides other than A nucleotides following the modified poly(A) tail, preferably one G nucleotide. This can prolong the lifetime and thus the duration of action of the produced polyribonucleotide when it is brought into a cell for example.

As regards the 5' UTR, the coding sequence, the 3' UTR, and the modified poly(A) tail the same applies as it has been described above. Moreover, also the other features of such genetic elements can be as described above.

The polyribonucleotide according to the present invention can be produced by any method known in the art. Preferably, the polyribonucleotide is transcribed in vitro using the DNA sequence according to the present invention as a template. In vitro transcription requires a purified linear DNA template containing a promoter, ribonucleotide triphosphates, a buffer system, and an appropriate RNA polymerase such as a T7 RNA polymerase. Hence, the DNA plasmid according to the invention is generally obtained by cell lysis and purified. The purified DNA plasmid is then cut, for example using a site-specific restriction enzyme, i) before the promoter preceding the first nucleotide sequence and ii) directly after the second nucleotide sequence encoding the modified poly(A) tail or, in case of additional nucleotides not being T nucleotides, directly after said additional nucleotides, preferably after one C nucleotide. The obtained linear template sequence is then used for the in vitro transcription of the polyribonucleotide according to the present invention in the presence of A, C, G, and U nucleotides using standard lab protocols. As the template is cut at the positions i) and ii), the template for transcription ends exactly with the desired modified poly(A) tail or the desired additional nucleotide that is not a T nucleotide. Hence, RNA polymerases can be used that do have or that do not have the ability to terminate transcription at a given position as for example, thus allowing run-off transcription. Thus, cutting the DNA plasmid at position i) and ii) and using the generated nucleotide sequence as a template for transcription, preferably for in vitro transcription, ensures the synthesis of polyribonucleotides according to the present invention comprising an mRNA molecule and a modified poly(A) tail of defined length. Quantity and quality of the in vitro transcribed polyribonucleotides can be measured for example by spectrophotometry, capillary electrophoresis and/or sequencing.

In a preferred embodiment, the produced polyribonucleotide is further modified by enzymatically adding a 5' cap such as a C1-m7G cap or an m7GpppG cap. This might be advantageous for adjusting and/or extending the duration of action of the polyribonucleotide in a cell.

In some embodiments of the present invention the polyribonucleotide is produced by in vitro transcription in the presence of unmodified and/or modified nucleotides. In other words, a polyribonucleotide as described above can be synthesized by in vitro transcription using at least a DNA sequence comprising a nucleotide sequence encoding an mRNA molecule and a nucleotide sequence encoding a modified poly(A) tail according to the present invention as a template using unmodified and/or modified nucleotides.

The term "unmodified nucleotide" used herein refers to A, C, G, T, and U nucleotides as described above. Particularly, in case of the in vitro transcription of a polyribonucleotide said term refers to A, C, G, and U nucleotides. The latter four are referred to herein as the four nucleotide types comprised in a polyribonucleotide.

The term "modified nucleotide" used herein refers to any naturally occurring or chemically synthesized isomers of A, C, G, T, and U nucleotides as well as to any naturally occurring or chemically synthesized analogs, alternative or modified nucleotide or isomer thereof having for example chemical modifications or substituted residues. Modified nucleotides can have a base modification and/or a sugar modification. Modified nucleotides can also have phosphate group modifications, e.g., with respect to the five prime cap of polyribonucleotides comprising a sequence which encodes a protein. Modified nucleotides also include nucleotides that are synthesized post-transcriptionally by covalent modification of the nucleotides. Further, any suitable mixture of non-modified and modified nucleotides is possible. A non-limiting number of examples of modified nucleotides can be found in the literature (e.g. Cantara et al., Nucleic Acids Res, 2011, 39(Issue suppl_1):D195-D201; Helm and Alfonzo, Chem Biol, 2014, 21(2):174-185; Carell et al., Angew Chem Int Ed Engl, 2012, 51(29):7110-31) and some preferable modified nucleotides are mentioned exemplarily in the following based on their respective nucleoside residue: 1-methyladenosine, 2-methylthio-N6-hydroxynorvalyl carbamoyladenosine, 2-methyladenosine, 2-O-ribosylphosphate adenosine, N6-methyl-N6-threonylcarbamoyladenosine, N6-acetyladenosine, N6-glycinylcarbamoyladenosine, N6-isopentenyladenosine, N6-methyladenosine, N6-threonylcarbamoyladenosine, N6,N6-d imethyladenosine, N6-(cis-hydroxyisopentenyl)adenosine, N6-hydroxynorvalylcarbamoyladenosine, 1,2-O-dimethyladenosine, N6,2-O-dimethyladenosine, 2-O-methyladenosine, N6,N6,0-2-trimethyladenosine, 2-methylthio-N6-(cis-hydroxyisopentenyl)adenosine, 2-methylthio-N6-methyladenosine, 2-methylthio-N6-isopentenyladenosine, 2-methylthio-N6-threonyl carbamoyladenosine, N6-2-methylthio-N6-threonyl carbamoyladenosine, 2-methylthio-N6-(cis-hydroxyisopentenyl)adenosine, 7-methyladenosine, 2-methylthio-adenosine, 2-methoxy-adenosine, 2"-amino-2"-deoxyadenosine, 2"-azido-2"-deoxyadenosine, 2"-fluoro-2"-deoxyadenosine, 2-aminopurine, 2,6-diaminopurine, 7-deaza-adenosine, 7-deaza-8-aza-adenosine, 7-deaza-2-aminopurine, 7-deaza-8-aza-2-aminopurine, 7-deaza-2,6-diaminopurine, 7-deaza-8-aza-2,6-diaminopurine; 2-thiocytidine, 3-methylcytidine, N4-acetylcytidine, 5-formylcytidine, N4-methylcytidine, 5-methylcytidine, 5-hydroxymethylcytidine, 5-hydroxycytidine, lysidine, N4-acetyl-2-0-methylcytidine, 5-formyl-2-0-methylcytidine, 5,2-O-dimethylcytidine, 2-O-methylcytidine, N4,2-0-dimethylcytidine, N4,N4,2-0-trimethylcytidine, isocytidine, pseudocytidine, pseudoisocytidine, 2-thio-cytidine, 2"-methyl-2"-deoxycytidine, 2"-amino-2"-deoxycytidine, 2"-fluoro-2"-deoxycytidine, 5-iodocytidine, 5-bromocytidine and 2"-azido-2"-deoxycytidine, 2'-amino-2'-deoxycytidine, 2'-fluor-2'-deoxycytidine, 5-aza-cytidine, 3-methyl-cytidine, 1-methyl-pseudoisocytidine, pyrrolo-cytidine, pyrrolo-pseudoisocytidine, 2-thio-5-methyl-cytidine, 4-thio-pseudoisocytidine, 4-thio-I-methyl-pseudoisocytidine, 4-thio-1-methyl-1-deaza-pseudoisocytidine, 1-methyl-1-deaza-pseudoisocytidine, 2-methoxy-cytidine, 2-methoxy-5-methyl-cytidine, 4-methoxy-pseudoisocytidine, 4-methoxy-1-methyl-pseudoisocytidine, zebularine,5-aza-zebularine, 5-methyl-zebularine, 5-aza-2-thio-zebularine, 2-thio-zebularine; 1-methylguanosine, N2,7-dimethylguanosine, N2-methylguanosine, 2-O-ribosylphosphate guanosine, 7-methylguanosine, hydroxywybutosine, 7-aminomethyl-7-deazaguanosine, 7-cyano-7-deazaguanosine, N2,N2-dimethylguanosine, N2,7,2-0-trimethylguanosine, N2,2-0-dimethylguanosine, 1,2-0-dimethylguanosine, 2-0-methylguanosine, N2,N2,2-0-trimethylguanosine, N2,N2J-trimethylguanosine, isoguanosine; 4-demethylwyosine, epoxyqueuosine, undermodified hydroxywybutosine, methylated undermodified hydroxywybutosine, isowyosine, peroxywybutosine, galactosyl-queuosine, mannosyl-queuosine, queuosine, archaeosine, wybutosine, methylwyosine, wyosine, 7-am inocarboxypropyldemethylwyosine, 7-aminocarboxypropylwyosine, 7-am inocarboxypropylwyosine methylester, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, 8-oxo-guanosine, 7-methyl-8-oxo-guanosine, 1-methyl-6-thio-guanosine, N2-methyl-6-thio-guanosine, N2,N2-dimethyl-6-thio-guanosine, N1-methylguanosine, 2"-amino-3"-deoxyguanosine, 2"-azido-2"-deoxyguanosine, 2"-fluoro-2"-deoxyguanosine; 2-thiouridine, 3-(3-amino-3-carboxypropyl)uridine, 3-methyluridine, 4-thiouridine, 5-methyl-2-thiouridine, 5-methylaminomethyluridine, 5-carboxymethyluridine, 5-carboxymethylaminomethyluridine, 5-hydroxyuridine, 5-methyluridine, 5-taurinomethyluridine, 5-carbamoylmethyluridine, 5-(carboxyhydroxymethyl)uridine methyl ester, dihydrouridine, 5-methyldihydrouridine, 5-methylaminomethyl-2-thiouridine, 5-(carboxyhydroxymethyl)uridine, 5-(carboxyhydroxymethyl)-2'-O-methyluridine methyl ester, 5-(isopentenylaminomethyl)uridine, 5-(isopentenylaminomethyl)-2-thiouridine, 3,2-O-d methyluridine, 5-carboxymethylaminomethyl-2-O-methyluridine, 5-carbamoylhydroxymethyluridine, 5-carbamoylmethyl-2-0-methyluridine, 5-carbamoylmethyl-2-thiouridine, 5-methoxycarbonylmethyl-2-O-methyluridine, 5-(isopentenylaminomethyl)-2-O-methyluridine, 5,2-0-dimethyluridine, 2-O-methyluridine, 2-O-methyl-2-thiorudine, 2-thio-2-O-methyluridine, uridine 5-oxyacetic acid, 5-methoxycarbonylmethyluridine, uridine 5-oxyacetic acid methyl ester, 5-methoxyuridine, 5-aminomethyl-2-thiouridine, 5-carboxymethylaminomethyl-2-thiouridine, 5-methylaminomethyl-2-selenouridine, 5-methoxycarbonylmethyl-2-thiouridine, 5-taurinomethyl-2-thiouridine, pseudouridine, 1-methyl-3-(3-amino-3-carboxypropyl) pseudouridine, 1-methylpseudouridine, 3-methylpseudouridine, 2-0-methylpseudouridine, 5-formyluridine, 5-aminomethyl-2-geranyluridine, 5-taurinomethyluridine, 5-iodouridine, 5-bromouridine, 2"-methyl-2"-deoxyuridine, 2"-amino-2"-deoxyuridine, 2"-azido-2"-deoxyuridine, and 2"-fluoro-2"-deoxyuridine; inosine, 1-methylinosine, 1,2-0-dimethylinosine and 2-0-methylinosine, 5-aza-uridine, 2-thio-5-aza-uridine, 4-thio-pseudouridine, 2-thio-pseudouridine, 5-carboxymethyl-uridine, 1-carboxymethyl-pseudouridine, 5-propynyl-uridine, 1-propynyl-pseudouridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine; most preferably pseudo-uridine, N1-methyl-pseudo-uridine, 2"-fluoro-2"-deoxycytidine, 5-iodocytidine, 5-methylcytidine, 2-thiouridine, 5-iodouridine and/or 5-methyl-uridine. The term "modified nucleotide" comprises nucleotides containing isotopes such as deuterium. The term "isotope" refers to an element having the same number of protons but different number of neutrons resulting in different mass numbers. Thus, isotopes of hydrogen for example are not limited to deuterium, but include also tritium. Furthermore, the polyribonucleotide can also contain isotopes of other elements including for example carbon, oxygen, nitrogen and phosphor. It is also possible that modified nucleotides are deuterated or contain another isotope of hydrogen or of oxygen, carbon, nitrogen or phosphor.

In case a polyribonucleotide according to the present invention is produced by in vitro transcription in the presence of four nucleotide types, i.e. A, C, G, and U nucleotides, the total number of modified nucleotide types can be 0, 1, 2, 3, or 4. In other words, in some embodiments, at least one nucleotide of one nucleotide type, e.g. at least one U nucleotide, can be a modified nucleotide. In some embodiments, at least one nucleotide of in total two nucleotide types, e.g. at least one U nucleotide and at least one C nucleotide, can be a modified nucleotide. In some embodiments, at least one nucleotide of in total three nucleotide types, e.g. at least one G nucleotide, at least one U nucleotide and at least one C nucleotide, can be a modified nucleotide. In some embodiments, at least one nucleotide of all four nucleotide types can be a modified nucleotide. In all these embodiments one or more nucleotides per nucleotide type can be modified, the percentage of said modified nucleotides of per nucleotide type being 0%, 2.5%, 5%, 7.5%, 10%, 15%, 20%, 25%, 30%, 35%, 40%, 45%, 50%, 55%, 60%, 65%, 70%, 75%, 80%, 85%, 90% or 100%.

In some embodiments, the total percentage of modified nucleotides comprised in the polyribonucleotide according to the present invention is 0%, 2.5%, 5%, 7.5%, 10%, 15%, 20%, 25%, 30%, 35%, 40%, 45%, 50%, 55%, 60%, 65%, 70%, 75%, 80%, 85%, 90% or 100%.

Preferably, the polyribonucleotide according the invention is characterized in that 5 to 30% of the U nucleotides and 5 to 30% of the C nucleotides are modified. Said modified U nucleotides are preferably 5-ioduridine and said modified C nucleotides are preferably 5-iodcytidine.

More preferably, the polyribonucleotide according the invention is characterized in that 7.5 to 25% of the U nucleotides and 7.5 to 25% of the C nucleotides are modified. Said modified U nucleotides are preferably 5-ioduridine and said modified C nucleotides are preferably 5-iodcytidine.

The present invention further relates to a polyribonucleotide obtainable by any of the methods described above.

As described above, the polyribonucleotide according to the present invention comprises a 5' UTR, a coding sequence, optionally a 3' UTR, and a modified poly(A) tail as encoded by the first and the second nucleotide sequence. Preferably, the polyribonucleotide comprises a 5' UTR with at least one RBS and/or IRES, a coding sequence with optimized codons, optionally a 3' UTR with at least one regulatory sequence, and a modified poly(A) tail. Furthermore, the polyribonucleotide can optionally comprise an additional nucleotide other than A nucleotides following the modified poly(A) tail, preferably one G nucleotide.

As regards the polyribonucleotide and the methods for obtaining said polyribonucleotide the same applies as described above in connection with the nucleotide sequence which encodes an mRNA molecule and the nucleotide sequence which encodes a modified poly(A) tail, the mRNA molecule and the modified poly(A) tail as well as methods of producing a polyribonucleotide comprising a sequence encoding an amino acid sequence and a modified poly(A) tail according to the present invention. Moreover, also the other features of such a polyribonucleotide can be as described above.

In some embodiments the polyribonucleotide as described above comprises one or more types of modified nucleotides. This might be advantageous for reducing immunogenicity in case of transfecting a cell with said polyribonucleotide. Furthermore, it might be advantageous for enhancing the amount of amino acid sequence that can be obtained by said polyribonucleotide in a cell.

As regards the polyribonucleotide and the methods for obtaining said polyribonucleotide the same applies as described above in connection with the nucleotide sequence which encodes an mRNA molecule and the nucleotide sequence which encodes a modified poly(A) tail, the mRNA molecule and the modified poly(A) tail as well as methods of producing a polyribonucleotide comprising a sequence encoding an amino acid sequence and a modified poly(A) tail using modified nucleotides according to the present invention. Moreover, also the other features of such a polyribonucleotide can be as described above.

The present invention further relates to a pharmaceutical composition containing a polyribonucleotide as described above together with a pharmaceutically acceptable carrier. The polyribonucleotide is preferably included in an effective amount, i.e. an amount sufficient to induce a detectable therapeutic response in the subject to which the pharmaceutical composition is to be administered. The polyribonucleotide or the pharmaceutical composition of the invention can be in sterile aqueous or non-aqueous solutions, suspensions, and emulsions as well as creams and suppositories, but can also have the form of powders, tablets or aerosols.

The term "pharmaceutically acceptable carrier" used herein refers to chemical compounds, materials, ingredients, and/or compositions, which are, within the scope of sound medical judgment, suitable for use in contact with the tissues of human beings and animals without excessive toxicity, irritation, allergic response, or other problem or complication, commensurate with a reasonable benefit/risk ratio. Thus, a pharmaceutically acceptable carrier is an inactive substance formulated alongside the pharmaceutically active substance for facilitating its handling in view of dosage, adsorption, solubility or pharmacokinetic considerations.

Examples of suitable pharmaceutical acceptable carriers are well known in the art and include phosphate buffered saline solutions, buffer, water, emulsions, such as oil/water emulsions, various types of wetting agents, and sterile solutions. In particularly, aqueous carriers include water, alcoholic/aqueous solutions, emulsions or suspensions, including saline and buffered media. Examples of non-aqueous solvents are propylene glycol, polyethylene glycol, vegetable oils such as olive oil, and organic esters such as ethyl oleate. Further examples of pharmaceutically acceptable carriers include but are not limited to saline, Ringer's solution and dextrose solution, citrate, phosphate, and other organic acids; salt-forming counter-ions, e.g. sodium and potassium; low molecular weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g., polyoxyethylene sorbitan monolaurate, available on the market with the commercial name Tween, propylene glycol, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol). Suitable pharmaceutically acceptable carriers and their formulations are described in greater detail in Remington's Pharmaceutical Sciences, 17th ed., 1985, Mack Publishing Co. Furthermore, preservatives, stabilizers and other additives can also be present such as, for example, antimicrobials, anti-oxidants, chelating agents, and inert gases, nanosystems or liposomes, and the like.

The pharmaceutical composition of the present invention can be administered via a large range of classes of forms of administration known to the skilled person, such as needle injection, the use of inhalators, creams, foams, gels, lotions and ointments. Dose and duration of action depend on the function which said polyribonucleotide is to fulfill and have to be deliberately adjusted in each case. The duration of action will be as long as possible for example, if said polyribonucleotide is used for the chronic therapy of a disease due to a deficient gene, while with other indications it can be adjusted to a specific time window. Furthermore, systemic administration of said one or more polyribonucleotides as described above is possible.

As regards the polyribonucleotide the same applies as described above in connection with the nucleotide sequence which encodes an mRNA molecule and the nucleotide sequence which encodes a modified poly(A) tail as well as methods of producing a polyribonucleotide comprising a sequence encoding an amino acid sequence and a modified poly(A) tail and polyribonucleotides according to the present invention. Moreover, also the other features of such a polyribonucleotide can be as described above.

FIG. 1: Quantification of poly(A) tail recombination based on the percentage of recombinant clones for $poly(A)_{120}$, $poly(A)_{3\times40\_6}$ and $poly(A)_{2\times60\_6}$ constructs.

Figure 2:
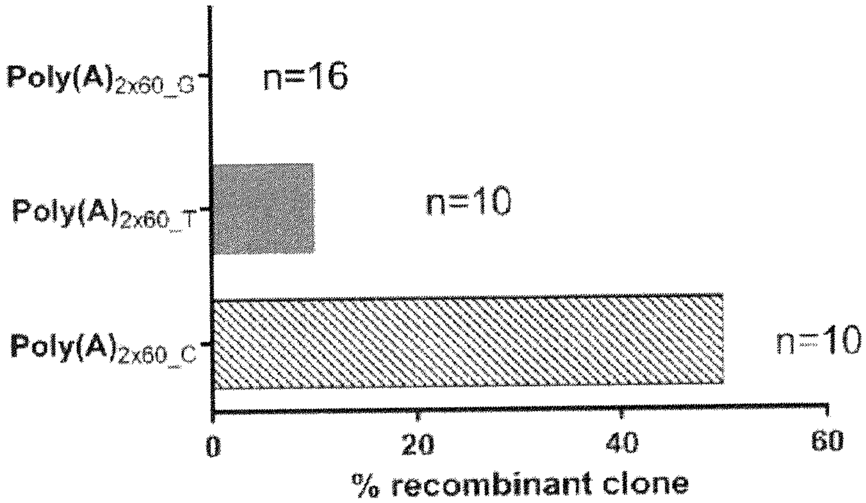

FIG. 2: Quantification of poly(A) tail recombination based on the percentage of recombinant clones using different one nucleotide spacer.

Figure 3:
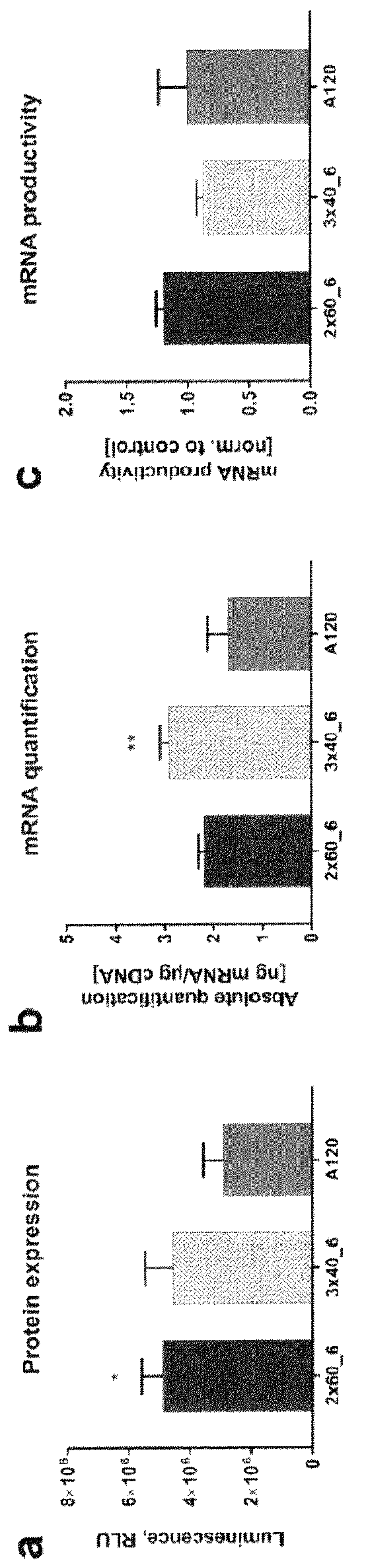

FIG. 3: Determination of luciferase protein activity and mRNA decay kinetics of different poly(A) constructs 24 h post-transfection (250 ng/well) in A549 cells. (a) Luciferase activity in protein lysates from A549 cells transfected with different poly(A) constructs. (b) Luciferase mRNA quantification in A549 cells. (c) mRNA productivity was calculated by dividing the luciferase luminescence values (RLU; a) by the mRNA amounts (real time qPCR data; b) and normalizing these ratios to those observed with $poly(A)_{120}$ construct. Statistical significance was assessed by two-way ANOVA test with p-values: *p<0.5, p<0.01, *p<0.001, ****p<0.0001, n=6.

Figure 4:
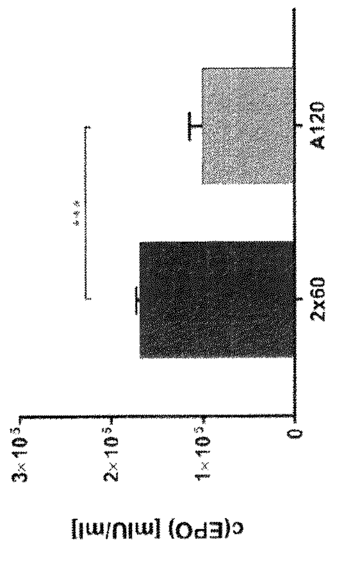

FIG. 4: Quantification of secreted human erythropoietin (hEPO) protein levels as measured via ELISA in supernatants from HEK293 cells transfected either with $poly(A)_{120}$ or $poly(A)_{2\times60\_6}$ constructs 24 h post-transfection (250 ng/well). Values represent mean±standard deviation of three replicates. Statistical significance was assessed by two-way ANOVA test with p-values: p<0.01, *p<0.001, n=3.

Figure 5:
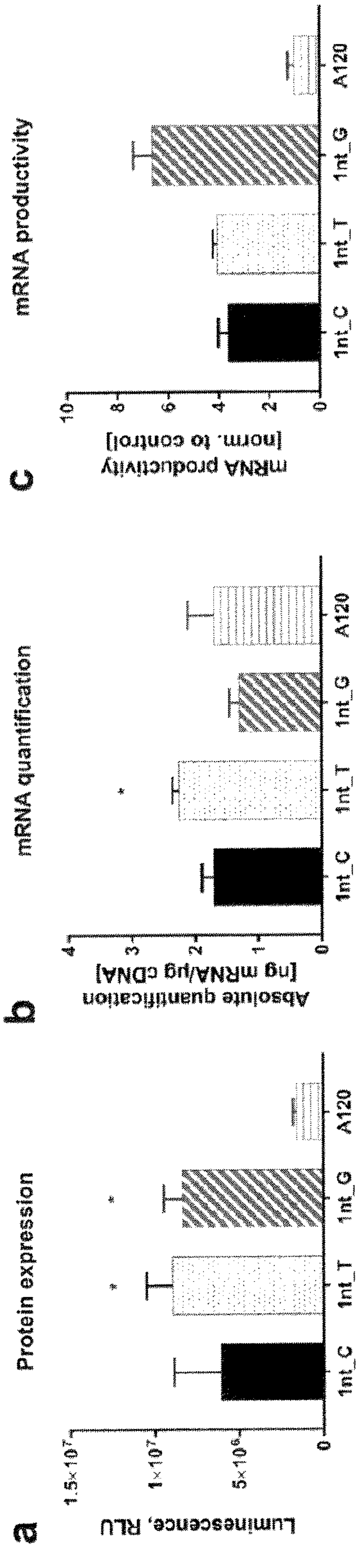

FIG. 5: Determination of luciferase protein activity and mRNA quantification of different poly(A) tail constructs 24 h post-transfection (250 ng/well) in A549 cells. (a) Luciferase activity in protein lysates from A549 cells transfected with different poly(A) tail constructs. (b) Luciferase mRNA quantification in A549 cells transfected with different poly (A) tail constructs. (c) Luciferase mRNA productivity was calculated by dividing the luciferase luminescence values (RLU; a) by the mRNA amounts (real time qPCR data; b) and normalizing these ratios to those observed with the $poly(A)_{120}$ construct. Statistical significance was assessed by two-way ANOVA test with p-values: *p<0.5, ****p<0.0001, n=6.

Other aspects and advantages of the invention will be described in the following examples, which are given for purposes of illustration and not by way of limitation. Each publication, patent, patent application or other document cited in this application is hereby incorporated by reference in its entirety.

EXAMPLES

Methods and materials are described herein for use in the present disclosure; other, suitable methods and materials known in the art can also be used. The materials, methods, and examples are illustrative only and not intended to be limiting.

Abbreviations used herein and their respective descriptions are listed in Table 2.

TABLE 2

| Abbreviation | Description |
|---|---|
| A | Nucleotide with an adenine residue |
| C | Nucleotide with an cytosine residue |
| ° C. | Degree Celsius |
| ELISA | Enzyme-linked Immunosorbent Assay |
| FA | Fragment Analyzer |
| G | Nucleotide with an guanine residue |
| h | Hour(s) |
| hIL-6 | Human interleukin 6 |
| min | Minutes |
| mRNA | Messenger ribonucleic acid |
| n | Total number of clones with a particular poly(A) tail sequence |
| n/a | Not applicable |
| ND | NanoDrop |

TABLE 2-continued

| Abbreviation | Description |
|---|---|
| nm | Nanometer |
| nt | Nucleotide(s) |
| poly(A)$_{120}$ | Nucleotide sequence encoding a poly(A) tail without S element consisting of 120 A nucleotides |
| poly(A)$_{3\times40\_6}$ | Nucleotide sequence encoding a poly(A) tail consisting of three A elements each consisting of 40 A nucleotides with any two A elements separated by a 6 nt long S element as defined in Table 6 |
| poly(A)$_{2\times60\_6}$ | Nucleotide sequenceen coding a poly(A) tail consisting of two A elements consisting of 60 A nucleotides each and separated by a 6 nt long S element as defined in Table 6 |
| poly(A)$_{2\times60\_C}$ | Nucleotide sequence encoding a poly(A) tail consisting of two A elements consisting of 60 A nucleotides each and separated by a C nucleotide |
| poly(A)$_{2\times60\_G}$ | Nucleotide sequence encoding a poly(A) tail consisting of two A elements, consisting of 60 A nucleotides each and separated by a G nucleotide |
| poly(A)$_{2\times60\_T}$ | Nucleotide sequence encoding a poly(A) tail consisting of two A elements consisting of 60 A nucleotides each and separated by a T nucleotide |
| qPCR | Quantitative real-time polymerase chain reaction |
| RLU | Relative light unit |
| T | Nucleotide with an thymine residue |
| U | Nucleotide with an uracile residue |
| % | Percent |

Material and Methods

Materials, Devices, Software, and Test System Used

Materials are listed in Table 3.

TABLE 3

| Material | Supplier | Cat# |
|---|---|---|
| pUC57-Kanamycin vector | GenScript | n/a |
| Oligonucleotides | IDT | n/a |
| Annealing buffer | Ethris GmbH | n/a |
| Tris HCl | Roth | 9090.1 |
| NaCl | Roth | 9265.1 |
| EDTA | Roth | 8040.1 |
| Phusion High-fidelity PCR master mix | Thermo Fisher Scientific | F531S |
| $MgCl_2$ | Roth | KK36.2 |
| DMSO | Sigma Aldrich | 67-68-5 |
| NucleoSpin Gel and PCR Clean-Up | Macherey-Nagel | 740609.250 |
| Mini prep kit | Macherey-Nagel | 740588.250 |
| Maxi Prep kit | Macherey-Nagel | 740414.10 |
| Agarose | Sigma Aldrich | A9539 |
| BglII | Thermo Fisher Scientific | FD0083 |
| NheI | Thermo Fisher Scientific | FD0973 |
| BstBI | Thermo Fisher Scientific | FD0124 |
| Chloroform | Sigma Aldrich | 288306 |
| Firefly luciferase coding region | Promega | n/a |
| d2EGFP coding region | Clontech | n/a |
| hEPO coding region | Pubmed | n/a |
| Ethanol | Roth | 5054.1 |
| T7 RNA polymerase | Thermo Fisher Scientific | EP0111 |
| Transcription buffer II | Ethris GmbH | n/a |
| RiboLock Rnase inhibitor | Thermo Fisher Scientific | EO0381 |
| Inorganic pyrophosphatase 1 | Thermo Fisher Scientific | EF0221 |
| Ribonucleotides | Jena Biosciences | NU-1010-NU-1013 |
| DNase I | Thermo Fisher Scientific | EN0525 |
| Ammonium acetate | Applichem | 131114.1210 |
| aqua ad injectabilia | B. Braun | 3703444 |
| Vaccinia Virus Capping Enzyme | NEB | M2080S |
| 1x capping buffer | NEB | M2080 |
| GTP | Jena Biosciences | NU-1012 |
| S-Methyladenosine | NEB | B9003S |
| mRNA Cap 2'-o-Methyltransferase | NEB | M0366S |
| Minimum Essential Media | GlutaMAX Gibco Life Technologies | 11095-080 |
| Glutamax | Gibco/Life Technologies | 35050061 |
| Fetal bovine serum | Gibco/Life Technologies | 10500064 |
| Penicillin/streptomycin | Gibco/Life Technologies | 15140122 |
| Lipofectamine ® 2000 | Thermo Fisher Scientific | 11668027 |

TABLE 3-continued

| Material | Supplier | Cat# |
|---|---|---|
| PBS | Gibco/Life Technologies | 10010023 |
| TritonX-100 | Sigma Aldrich | 9002-93-1 |
| BioRad protein assay dye reagent concentrate | Bio-Rad | 5000006 |
| Bovine serum albumin | Sigma Aldrich | A2058 |
| Propidium iodide | Sigma Aldrich | 11348639001 |
| TrypLE | Gibco/Life Technologies | 12604-013 |
| Single Shot Cell Lysis kit | Bio-Rad | 1725080 |
| iScript Select cDNA Synthesis kit | Bio-Rad | 1708896 |
| Universal Probe Library #29 | Roche | 4687612001 |

Devices are listed in Table 4.

TABLE 4

| Device | Supplier |
|---|---|
| Roche Light Cycler 96 | Roche Diagnostics |
| NanoDrop2000C | Thermo Fisher Scientific |
| Fragment Analyzer | Advanced Analytical |
| Humidified 5% CO2 incubator | Sanyo |
| InfiniteR 200 PRO | Tecan |
| Attune Acoustic Focusing Cytometer | Life Techologies |
| Gene Pulser II | Biorad |

Software is listed in Table 5.

TABLE 5

| Software | Provider |
|---|---|
| GraphPad Prism software (version 6) | GraphPad Software Inc. |
| Attune Cytometric Software (version 2.1) | Life Technologies |
| FlowJo (version 10) | FlowJo |
| LightCycler ® 96 (version 1.1) | Roche |
| PROSize 3.0 | Advanced analytical |

The test system is listed in Table 6.

TABLE 6

| Test System | Species | Strain | Thawed passage no. | Used passage no. | Supplier |
|---|---|---|---|---|---|
| Cell line | *E. coli* | *E. coli* DH10B strain | — | — | — |
| Cell line | Human | A549 (ACC-107) | 4-7 | Up to 15 | DSMZ |
| Cell line | Human | HEK293 (ACC-305) | 4-7 | Up to 15 | DSMZ |

Plasmid Preparation

Synthetic poly(A) tail sequences were introduced to the pUC57-Kanamycin vector backbone either as annealed complementary oligonucleotides or fragments created by PCR-based strategy. A specific set of complementary oligonucleotides was designed for sequences comprising poly$(A)_{2\times60_6}$ constructs and poly$(A)_{3\times40_6}$ constructs and annealed. The synthetic poly(A) constructs of poly$(A)_{120}$, Poly$(A)_{2\times60_C}$, poly$(A)_{2\times60_G}$, and poly$(A)_{2X60_T}$ were created by PCR.

The two sets of complementary oligonucleotides were annealed in the following way: 100 μM of each oligonucleotide were mixed with 40 μl annealing buffer and incubated for 5 min at 95° C. (10 mM Tris HCl, 50 mM NaCl, 1 mM EDTA, pH 7.5). After the reaction, the mixture was let to cool down to room temperature before proceeding with restriction digestion (BglII-BstBI).

For the high performance of PCR reaction, Phusion High-fidelity PCR master mix was used. In addition to the master mix which contains 2× Phusion DNA Polymerase, nucleotides and optimized reaction buffer including $MgCl_2$, 0.5 μM of forward and reverse primer, 3% DMSO and 100 ng of template DNA were added to the reaction. The total volume of 25 μl per reaction was initially denatured at 98° C. for 30 sec, following by 30 cycles at 98° C. for 10 sec, annealing at 72° C. for 30 sec and extension at 72° C. for 30 sec/kb. The final extension was performed at 72° C. for 10 min. The size of the PCR product was confirmed on 1% agarose gel and the desired band was purified using Necleo-Spin Gel and PCR clean up kit. Purified PCR product was digested with Nhel-BstBI and stored at −20° C. till further use. After restriction enzyme digestion of annealed oligonucleotides (BglII-BstBI) and PCR fragments (Nhel-BstBI), the poly(A) tail constructs were cloned into accordingly digested pUC57-Kanamycin vectors comprising the coding region of choice (firefly luciferase, hEPO, d2EGFP).

A list of segmented poly(A) sequences and corresponding cloning strategy with PCR primer sets or oligonucleotides is shown in Table 7.

TABLE 7

| Construct | Strategy | PCR primer forward/Oligo I | PCR primer reverse/Oligo II |
|---|---|---|---|
| A120 | PCR | GTGACTGCTAGCTAATACGACTCACTAT AGGGAG (SEQ ID No: 1) | AGTCACTTCGAATTTTTTTTTTTTTTTTTT TTTTTTTTTTTTTTTTTTTTTTTTTTTTTTT TTTTTTTTTTTTTTTTTTTTTTTTTTTTTTT TTTTTTTTTTTTTTTTTTTTTTTTTTTTTTT TTTTTTTTTTTTTTAGATCTTTACACGGC GATCTTGCCGCCCTTC (SEQ ID No: 2) |
| 2x60_6 | Oligonucleotides | GTGACTAGATCTAAAAAAAAAAAAAAAAAA AAAAAAAAAAAAAAAAAAAAAAAAAAAAAA | AGTCACTTCGAATTTTTTTTTTTTTTTTTT TTTTTTTTTTTTTTTTTTTTTTTTTTTTTTT |

TABLE 7-continued

| Construct | Strategy | PCR primer forward/Oligo I | PCR primer reverse/Oligo II |
|---|---|---|---|
| | | AAAAAAAAAAAAAAATGCATAAAAAAAAAA<br>AAAAAAAAAAAAAAAAAAAAAAAAAAAAAA<br>AAAAAAAAAAAAAAAAAAAAAAATTCGAAG<br>TGACT (SEQ ID No: 3) | TTTTTTTTTTTTTATGCATTTTTTTTTTTT<br>TTTTTTTTTTTTTTTTTTTTTTTTTTTTTT<br>TTTTTTTTTTTTTTTTTTTAGATCTAGTC<br>AC (SEQ ID No: 4) |
| 3x40_6 | Oligonucleotides | GTGACTAGATCTAAAAAAAAAAAAAAAAAA<br>AAAAAAAAAAAAAAAAAAAAAAAAATGCAT<br>AAAAAAAAAAAAAAAAAAAAAAAAAAAAAA<br>AAAAAAAAAAAGATATCAAAAAAAAAAAAA<br>AAAAAAAAAAAAAAAAAAAAAAAAAAAAAT<br>TCGAAGTGACT (SEQ ID No: 5) | AGTCACTTCGAATTTTTTTTTTTTTTTTT<br>TTTTTTTTTTTTTTTTTTTTTTTGATATCT<br>TTTTTTTTTTTTTTTTTTTTTTTTTTTTTT<br>TTTTTTTTATGCATTTTTTTTTTTTTTTTT<br>TTTTTTTTTTTTTTTTTTTTTTTTTAGATC<br>TAGTCAC (SEQ ID No: 6) |
| 2x60_C | PCR | GTGACTGCTAGCTAATACGACTCACTAT<br>AGGGAG (SEQ ID No: 1) | AGTCACTTCGAATTTTTTTTTTTTTTTTT<br>TTTTTTTTTTTTTTTTTTTTTTTTTTTTTT<br>TTTTTTTTTTTTTGTTTTTTTTTTTTTTTT<br>TTTTTTTTTTTTTTTTTTTTTTTTTTTTTT<br>TTTTTTTTTTTTTTAGATCTTTACACGG<br>CGATCTTGCCGCCCTTC (SEQ ID No: 7) |
| 2x60_G | PCR | GTGACTGCTAGCTAATACGACTCACTAT<br>AGGGAG (SEQ ID No: 1) | AGTCACTTCGAATTTTTTTTTTTTTTTTT<br>TTTTTTTTTTTTTTTTTTTTTTTTTTTTTT<br>TTTTTTTTTTTTTCTTTTTTTTTTTTTTTT<br>TTTTTTTTTTTTTTTTTTTTTTTTTTTTTT<br>TTTTTTTTTTTTTTAGATCTTTACACGG<br>CGATCTTGCCGCCCTTC (SEQ ID No: 8) |
| 2x60_T | PCR | GTGACTGCTAGCTAATACGACTCACTAT<br>AGGGAG (SEQ ID No: 1) | AGTCACTTCGAATTTTTTTTTTTTTTTTT<br>TTTTTTTTTTTTTTTTTTTTTTTTTTTTTT<br>TTTTTTTTTTTTTATTTTTTTTTTTTTTTT<br>TTTTTTTTTTTTTTTTTTTTTTTTTTTTTT<br>TTTTTTTTTTTTTTAGATCTTTACACGG<br>CGATCTTGCCGCCCTTC (SEQ ID No: 9) |

Cloning into *E. coli*

The ligations were purified using chloroform-ethanol precipitation and electroporated into DH10B strain of *E. coli*. For electroporation, Gene Pulser II from Biorad was used. Electroporation conditions followed were: 25 μF, 200 ohms, 1.8 kV. Post electroporation, the bacteria were grown in 2 mL of LB-Medium at 30° C. for 1.5 hours. Subsequently, the culture was centrifuged at 5000 rpm for 10 min at room temperature. Supernatant was discarded and the pellet was resuspended in 200 μL of fresh LB-Medium. From this, 100 μL were plated in LB-Agar plates containing the appropriate antibiotic (Kanamycin at a final concentration of 50 μg/mL or Ampicillin at a final concentration of 100 μg/mL). The plates were incubated overnight at 30° C.

Plasmid Preparation Using Mini-Prep Kit

Clones were inoculated in LB-Medium containing the appropriate antibiotic (Kanamycin at a final concentration of 50 μg/mL or ampicillin at a final concentration of 100 μg/mL) and grown at 30° C. overnight in a bacterial shaker (250 rpm). Subsequently plasmids were isolated from the overnight cultures using Mini-Prep kit. Plasmids were tested for insert using restriction digestion and confirmed via sequencing. For the correct clones, glycerol stocks were prepared by adding 200 μL autoclaved glycerol to 800 μL of overnight bacterial culture. Glycerol stocks were stored at −80° C.

Plasmid Preparation Using Maxi-Prep Kit

Plasmid for RNA production was prepared using the Maxi-Prep kit. Glycerol stock from the desired clone(s) was inoculated in 5 mL of LB-Medium containing appropriate antibiotics (Kanamycin at final concentration of 50 μg/mL or Ampicillin at a final concentration of 100 μg/mL) and the culture was grown overnight at 30° C. in a bacterial shaker (250 rpm). 3 mL from this starter culture were used to inoculate 300 mL of LB-Medium containing appropriate antibiotic (Kanamycin at a final concentration of 50 μg/mL or Ampicillin at a final concentration of 100 μg/mL) which was subsequently incubated overnight at 30° C. in a bacterial shaker (250 rpm).Overnight culture was centrifuged at 5000 rpm, 4° C. for 30 min. Supernatant was discarded and the bacterial pellet was used to isolate the plasmid.

Generation of mRNA

To generate in vitro transcribed mRNA, plasmids were linearized by BstBI digestion and purified by chloroform extraction and ethanol precipitation. Purified linear plasmids were used as a template for in vitro transcription. Plasmid templates (0.5 μg/μl) were subjected to in vitro transcription using 3 U/μl T7 RNA polymerase, transcription buffer II, 1 U/μl RiboLock Rnase inhibitor, 0.015 U/μl inorganic pyrophosphatase 1 with a defined choice of ribonucleotides. The complete IVT-mix was incubated at 37° C. for 2 h. Afterwards, 0.01 U/μl DNase I was added for additional 45 min at 37° C. to remove the plasmid template. RNA was precipitated with ammonium acetate at a final concentration of 2.5 mM, followed by two washing steps with 70% ethanol. The pellet was re-suspended in aqua ad injectabilia. A C1-m7G cap structure was added enzymatically by 0.5 mM Vaccinia Virus Capping Enzyme to the 5' end of the previously denaturated transcript (1 mg/ml) at 80° C. for 5 min. The capping reaction mix also contained 1× capping buffer, 0.5 mM GTP, 0.2 mM S-Methyladenosine, 2.5 U/μl Mrna Cap 2'-o-Methyltransferase and 1 U/μl RiboLock Rnase Inhibitor. The capping mixture was incubated for 60 min at 37° C., followed by RNA precipitation with ammonium acetate at a final concentration of 2.5 mM and two washing steps with 70% ethanol. The pellet was re-suspended in aqua ad injectabilia.

RNA quality and concentration were measured spectrophotometrically on a NanoDrop2000C. Its correct size and purity were determined via automated capillary electrophoresis.

Cell Culture

A549 (ACC-107) and HEK293 (ACC-305) cells were purchased from DSMZ. All cells were cultivated in Minimum Essential Media (MEM) with Glutamax. Media were supplemented with 10% heat-inactivated fetal bovine serum (FBS) and 1 penicillin/streptomycin. Cells were cultured in a humidified 5% $CO_2$ incubator at 37° C.

In Vitro Transfection Both cell lines, A549 and HEK293, were transfected with 250 ng mRNA per well. A549 and HEK293 cells were seeded at the density of $2\times10^4$ cells/well and $4\times10^4$ cells/well, respectively, in a 96 well plate, for the purpose of firefly luciferase and hEPO ELISA assay. 24 hours post-seeding, cells were transfected using the commercial transfection reagent Lipofectamine® 2000. Complexes were prepared at a ratio of 2 µl Lipofectamine® 2000 per 1 µg mRNA.

The mRNA was diluted 1:20 in water, and Lipofectamine® 2000 1:10 separately in a serum-free MEM. mRNA was added to the Lipofectamine® 2000 solution followed by 20 min incubation time at RT. The concentration of the final mRNA/Lipofectamine® 2000 solution was 25 ng/µl, and a serial dilution 1:2 was performed. 10 µl of the complex solution was added to the cells and cells were incubated for 24 and 48 h, respectively. For every mRNA construct, replicates of three or six were prepared.

Flow Cytometry Analysis for d2EGFP

Cells were washed with PBS, detached with TrypLE, and re-suspended in flow cytometry buffer (PBS supplemented with 10% FBS). Shortly before measurement, cells were stained with propidium iodide for discrimination between live and dead cells (1 µg/mL). Live cells (>97%) were further gated to discriminate between d2EGFP-expressing cells and those that did not express. Analysis was performed on an Attune Acoustic Focusing Cytometer with Attune Cytometric Software (version 2.1) and FlowJo (version 10).

Firefly Luciferase Assay

For detection of firefly luciferase activity, the assay was performed 24 h post-transfection. At the appropriate time point, cells were washed with PBS, followed by addition of 100 µl of lysis buffer (25 mM Tris-HCl, 0.1% TritonX-100, pH 7.4). Cells were shaken for 20 min at room temperature. After lysation, 50 µl of the cell lysate was used to measure luciferase activity via photon luminescence emission for 5 s using InfiniteR 200 PRO. The protein amount in each sample was quantified in 5 µl of the cell lysate with BioRad protein assay, using bovine serum albumin as a standard. Luciferase values were normalized to the protein concentration.

RNA Isolation and Reverse Transcription

In order to determine the actual mRNA amount 24 h post-transfection, the cultured cells (A549, HEK293) were lysed and RNA was isolated according to the manufacturer's protocol using Single Shot Cell Lysis kit. From the lysates (1 µg of RNA), cDNA was synthesized using iScript Select cDNA Synthesis kit with oligo(dT) primers following the manufacturer's instructions. The synthesized cDNA was stored at −20° C.

Quantitative Real-Time Polymerase Chain Reaction (qPCR)

Real-time qPCR was performed with short hydrolysis probes for d2EGFP and luciferase targets (Universal Probe Library #37 and #29) on a Roche Light Cycler 96. The following primers for d2EGFP were used: 5'-cctgaagttcatctgcacca-3' and 5'-ctcgtgaccaccctgacc-3'; and for the luciferase target: 5'-acgccgagtacttcgagatg-3' and 5'-attcagcccatagcgcttc-3'. Absolute mRNA values were calculated by interpolation from the standard curve.

Statistical Analysis

Each experiment was performed with at least three technical replicates per sample. Results are shown as means±SD unless otherwise stated. Statistical analysis was performed using GraphPad Prism software (version 6). Data was tested for normal distribution using D'Agostino-Pearson omnibus normality test. Multiple comparisons were conducted by two-way ANOVA, followed by Sidak's test (pairwise comparison) or Dunett's test (many-to-one comparison). A p-value ≤0.05 was considered statistically significant.

Segmented Poly(A) Tails Drastically Reduce Bacterial Recombination

It was examined whether the use of segmented poly(A) tails affected the recombination of plasmids post transformation into *E. coli*. To test this, open reading frame sequences of different genes (luciferase, d2EGFP, hEPO) were combined with either of the three poly(A) constructs $poly(A)_{120}$, $poly(A)_{2\times60\_6}$, and $poly(A)_{3\times40\_6}$ and cloned into a pUC57-Kanamycin vector. Post transformation into *E. coli*, clones were screened for insert and positive clones containing the desired insert were additionally screened for the length of the respective poly(A) tail. For each of the three poly(A) tail constructs, the poly(A) tail was digested with restriction enzymes and the digestions were resolved on Fragment Analyzer (capillary gel electrophoresis) to measure the size of the respective poly(A) tail. Recombination in the poly(A)-tail was observed for more than 50% of the clones containing the homologous poly(A) tail $poly(A)_{120}$. By splitting the poly(A) tail into either $poly(A)_{3\times40\_6}$ or $poly(A)_{2\times60\_6}$, recombination in *E. coli* could be significantly reduced with most stable clones (<20% recombination) obtained with plasmids containing $poly(A)_{2\times60\_6}$ (FIG. 1; Table 8). This trend was observed for all three tested open reading frame sequences indicating that this reduction in recombination is sequence independent. The most favorable effect was observed for $poly(A)_{2\times60\_6}$ constructs with recombination 20% or less.

TABLE 8

| | Target genes | | |
|---|---|---|---|
| Poly(A) | Luc2 | d2EGFP | EPO |
| $Poly(A)_{2\times60\_6}$ | 56 | 10 | 15 |
| $Poly(A)_{3\times40\_6}$ | 10 | 10 | — |
| $Poly(A)_{120}$ | 11 | 10 | 16 |

Effect of a One Nucleotide Long Spacer within a Poly(A) Tail on Recombination

The effect of a one nucleotide long spacer in a $poly(A)_{2\times60}$ construct (C, T or G) on recombination in *E. coli* was examined by investigating clones comprising the open reading frame sequence of the firefly luciferase and the respective $poly(A)_{2\times60\_C}$, $poly(A)_{2\times60\_G}$, or $poly(A)_{2\times60\_T}$ construct. Interestingly, the constructs comprising G as a spacer in the poly(A) tail, did not recombine at all. A spacer with a single T recombined in 10% of cases, and the one with a C as a spacer nucleotide recombined in 50% of cases (FIG. 2), which, at first sight seems to be comparable to recombination efficiencies observed with A120 (FIG. 1) but is still significantly lower. This is evident from the following Table 9 which summarizes the recombination efficiencies observed for the constructs tested in FIGS. 1 and 2.

TABLE 9

| Poly(A) | Figure | n | Recombination rate |
|---|---|---|---|
| Poly(A)$_{2\times 60\_6}$ | 1 | 81 | 19% |
| Poly(A)$_{3\times 40\_6}$ | 1 | 20 | 35% |
| Poly(A)$_{120}$ | 1 | 37 | 54% |
| Poly(A)$_{2\times 60\_G}$ | 2 | 16 | 0% |
| Poly(A)$_{2\times 60\_T}$ | 2 | 10 | 10% |
| Poly(A)$_{2\times 60\_C}$ | 2 | 10 | 50% |

Effect of a Six Nucleotide Long Spacer on mRNA and Protein Levels

Luciferase protein and mRNA decay was investigated in A549 cells at 24 h post-transfection with luciferase mRNA, containing either a poly(A)$_{2\times 60\_6}$, poly(A)$_{3\times 40\_6}$ or poly(A)$_{120}$ construct. Use of the segmented poly(A)$_{2\times 60\_6}$ construct significantly increased protein levels post-transfection when compared to the poly(A)$_{120}$ benchmark (FIG. 3). No significant differences were observed between the mRNA amounts for the different poly(A) format containing luciferase mRNAs across modifications.

Further, the effects of poly(A) segmentation on transcription and translation of a physiological target was tested using human erythropoietin (hEPO) as a prototype of secretory proteins and short mRNAs (0.9 kb). The codon optimized sequence encoding hEPO was cloned into a pUC57-Kanamycin vector upstream of either a poly(A)$_{120}$ or a poly (A)$_{2\times 60\_6}$ construct. hEPO protein concentrations were determined via ELISA 24 h post-transfection (FIG. 4). A significant difference was observed between the two compared poly(A) tail constructs with the poly(A)$_{2\times 60\_6}$ construct resulting in significantly more protein compared to the standard poly(A)$_{120}$ construct.

Effect of a One Nucleotide Long Spacer on mRNA and Protein Levels

The effect of a single spacer nucleotide within a poly(A)$_{2\times 60}$-tail on protein expression and mRNA productivity was tested. Luciferase mRNA expression and protein activity was determined by transfecting A549 cells with mRNA constructs containing a single C, T, or G spacer nucleotide within the respective poly(A)$_{2\times 60}$-tail. As a benchmark, the standard poly(A)$_{120}$ construct was used. Between all three single nucleotide spacer constructs, there was no significant difference in protein expression, but all of them resulted in significantly more protein compared to the poly(A)$_{120}$ construct (FIG. 5). Calculating mRNA productivity, the construct with a C as a spacer appears to have the highest productivity overall. mRNA productivity of poly(A)$_{120}$ was significantly lower compared to that of any of the three tested segmented constructs poly(A)$_{2\times 60\_C}$, poly(A)$_{2X60\_G}$, poly(A)$_{2\times 60\_T}$.

The invention claimed is:

1. A DNA plasmid comprising a DNA sequence which contains:

(i) a first nucleotide sequence which encodes an mRNA molecule and, located downstream thereof, (ii) a second nucleotide sequence which encodes a modified poly (A) tail, wherein said second nucleotide sequence comprises:

(a) at least two A elements each defined as a nucleotide sequence consisting of 55 to 65 T nucleotides, and (b) at least one S element, each S element consisting of:

(b1) one nucleotide that is not a T nucleotide, or (b2) 2 to 10 nucleotides wherein each of the two terminal nucleotides of the 2 to 10 nucleotides is not a T nucleotide;

wherein any one of the at least one S elements consists of one C nucleotide or one A nucleotide wherein the total number of A elements is one more than the total number of S elements, and wherein any two A elements are separated by one S element.

2. The DNA plasmid of claim 1, wherein the number of A elements is two, three or four.

3. The DNA plasmid of claim 1, wherein the number of A elements is two and wherein said nucleotide sequences of the two A elements together have an overall length of 120 nucleotides.

4. The DNA plasmid of claim 3, wherein each A element has a length of 60 nucleotides.

5. The DNA plasmid of claim 1, wherein any one of the at least one S elements consists of one C nucleotide.

6. The DNA plasmid of claim 5, wherein the number of A elements is two and wherein said nucleotide sequences of the two A elements together have an overall length of 120 nucleotides.

7. The DNA plasmid of claim 1, each S element consisting of:

(b1) one nucleotide that is not a T nucleotide, or (b2) 2 to 6 nucleotides wherein each of the two terminal nucleotides of the 2 to 6 nucleotides is not a T nucleotide.

8. A bacterial host cell comprising the DNA plasmid of claim 1.

9. The bacterial host cell of claim 8, which is an *E. coli* cell.

10. The bacterial host cell of claim 9, wherein the *E. coli* cell is an *E. coli* recA cell.

11. A polyribonucleotide obtained by in vitro transcription of the DNA plasmid of claim 1.

12. The polyribonucleotide of claim 11, wherein the polyribonucleotide comprises one or more types of modified nucleotides.

13. A pharmaceutical composition containing the polyribonucleotide of claim 11 together with a pharmaceutically acceptable carrier.

14. A DNA plasmid comprising a DNA sequence which contains:

(i) a first nucleotide sequence which encodes an mRNA molecule and, located downstream thereof, (ii) a second nucleotide sequence which encodes a modified poly (A) tail, wherein said second nucleotide sequence comprises:

(a) four A elements each defined as a nucleotide sequence consisting of 55 to 65 T nucleotides, and (b) three S elements, each S element consisting of:

(b1) one nucleotide that is not a T nucleotide, or (b2) 2 to 10 nucleotides wherein each of the two terminal nucleotides of the 2 to 10 nucleotides is not a T nucleotide;

wherein any two A elements are separated by one S element, and wherein said nucleotide sequences of the four A elements together have an overall length of 240 nucleotides.

15. The DNA plasmid of claim 14, wherein each A element has a length of 60 nucleotides.

16. A bacterial host cell comprising the DNA plasmid of claim 14.

17. A polyribonucleotide obtained by in vitro transcription of the DNA plasmid of claim 14.

18. A DNA plasmid comprising a DNA sequence which contains:

(i) a first nucleotide sequence which encodes an mRNA molecule and, located downstream thereof, (ii) a second nucleotide sequence which encodes a modified poly(A) tail, wherein said second nucleotide sequence comprises:

(a) at least two A elements each defined as a nucleotide sequence consisting of 55 to 65 T nucleotides, and;

(b) at least one S element, wherein each S element consists of six nucleotides, wherein each of the two terminal nucleotides of the six nucleotides is not a T nucleotide, wherein the total number of A elements is one more than the total number of S elements, and wherein any two A elements are separated by one S element.

* * * * *

SEQUENCE LISTING

<160> NUMBER OF SEQ ID NOS: 9

<210> SEQ ID NO 1
<211> LENGTH: 34
<212> TYPE: DNA
<213> ORGANISM: Artificial Sequence
<220> FEATURE:
<223> OTHER INFORMATION: PCR primer forward / Oligo I

<400> SEQUENCE: 1
gtgactgcta gctaatacga ctcactatag ggag 34

<210> SEQ ID NO 2
<211> LENGTH: 163
<212> TYPE: DNA
<213> ORGANISM: Artificial Sequence
<220> FEATURE:
<223> OTHER INFORMATION: PCR primer reverse / Oligo II

<400> SEQUENCE: 2
agtcacttcg aatttttttt tttttttttt tttttttttt tttttttttt tttttttttt 60
tttttttttt tttttttttt tttttttttt tttttttttt tttttttttt tttttttttt 120
tttttttttt ttagatcttt acacggcgat cttgccgccc ttc 163

<210> SEQ ID NO 3
<211> LENGTH: 150
<212> TYPE: DNA
<213> ORGANISM: Artificial Sequence
<220> FEATURE:
<223> OTHER INFORMATION: PCR primer forward /Oligo I

<400> SEQUENCE: 3
gtgactagat ctaaaaaaaa aaaaaaaaaa aaaaaaaaaa aaaaaaaaaa aaaaaaaaaa 60
aaaaaaaaaa aaatgcataa aaaaaaaaaa aaaaaaaaaa aaaaaaaaaa aaaaaaaaaa 120
aaaaaaaaaa aaaaaaaatt cgaagtgact 150

<210> SEQ ID NO 4
<211> LENGTH: 150
<212> TYPE: DNA
<213> ORGANISM: Artificial Sequence
<220> FEATURE:
<223> OTHER INFORMATION: PCR primer reverse / Oligo II

<400> SEQUENCE: 4
agtcacttcg aatttttttt tttttttttt tttttttttt tttttttttt tttttttttt 60
tttttttttt ttatgcattt tttttttttt tttttttttt tttttttttt tttttttttt 120
tttttttttt ttttttttag atctagtcac 150

<210> SEQ ID NO 5
<211> LENGTH: 156
<212> TYPE: DNA
<213> ORGANISM: Artificial Sequence
<220> FEATURE:
<223> OTHER INFORMATION: PCR primer forward / Oligo I

<400> SEQUENCE: 5
gtgactagat ctaaaaaaaa aaaaaaaaaa aaaaaaaaaa aaaaaaaaaa aaatgcataa 60
aaaaaaaaaa aaaaaaaaaa aaaaaaaaaa aaaaaaaaga tatcaaaaaa aaaaaaaaaa 120
aaaaaaaaaa aaaaaaaaaa aaaattcgaa gtgact 156

<210> SEQ ID NO 6
<211> LENGTH: 156
<212> TYPE: DNA
<213> ORGANISM: Artificial Sequence
<220> FEATURE:
<223> OTHER INFORMATION: PCR primer reverse /Oligo II

<400> SEQUENCE: 6
agtcacttcg aatttttttt tttttttttt tttttttttt tttttttttt ttgatatctt 60
tttttttttt tttttttttt tttttttttt ttttttttat gcattttttt tttttttttt 120
tttttttttt tttttttttt ttttagatct agtcac 156

<210> SEQ ID NO 7
<211> LENGTH: 164
<212> TYPE: DNA
<213> ORGANISM: Artificial Sequence
<220> FEATURE:
<223> OTHER INFORMATION: PCR primer reverse / Oligo II

<400> SEQUENCE: 7
agtcacttcg aatttttttt tttttttttt tttttttttt tttttttttt tttttttttt 60
tttttttttt ttgttttttt tttttttttt tttttttttt tttttttttt tttttttttt 120
tttttttttt tttagatctt tacacggcga tcttgccgcc cttc 164

<210> SEQ ID NO 8
<211> LENGTH: 164
<212> TYPE: DNA
<213> ORGANISM: Artificial Sequence
<220> FEATURE:
<223> OTHER INFORMATION: PCR primer reverse / Oligo II

<400> SEQUENCE: 8
agtcacttcg aatttttttt tttttttttt tttttttttt tttttttttt tttttttttt 60
tttttttttt ttcttttttt tttttttttt tttttttttt tttttttttt tttttttttt 120
tttttttttt tttagatctt tacacggcga tcttgccgcc cttc 164

-continued

```
<210> SEQ ID NO 9
<211> LENGTH: 164
<212> TYPE: DNA
<213> ORGANISM: Artificial Sequence
<220> FEATURE:
<223> OTHER INFORMATION: PCR primer reverse / Oligo II

<400> SEQUENCE: 9

agtcacttcg aatttttttt tttttttttt tttttttttt tttttttttt tttttttttt      60

tttttttttt ttattttttt tttttttttt tttttttttt tttttttttt tttttttttt     120

tttttttttt tttagatctt tacacggcga tcttgccgcc cttc                     164
```